US012735500B2

(12) United States Patent
Cai et al.

(10) Patent No.: US 12,735,500 B2
(45) Date of Patent: Sep. 15, 2026

(54) ANTI-CD47 ANTIBODY AND USES THEREOF

(71) Applicant: HUTCHISON MEDIPHARMA LIMITED, Shanghai (CN)

(72) Inventors: Yu Cai, Shanghai (CN); Yizhen Yang, Shanghai (CN); Xiong Li, Shanghai (CN); Xianwen Yang, Shanghai (CN); Yongxin Ren, Shanghai (CN); Wei-Guo Su, Shanghai (CN)

(73) Assignee: HUTCHISON MEDIPHARMA LIMITED, Shanghai (CN)

( * ) Notice: Subject to any disclaimer, the term of this patent is extended or adjusted under 35 U.S.C. 154(b) by 908 days.

(21) Appl. No.: 17/995,810

(22) PCT Filed: Apr. 11, 2021

(86) PCT No.: PCT/CN2021/086339
§ 371 (c)(1),
(2) Date: Oct. 7, 2022

(87) PCT Pub. No.: WO2021/204281
PCT Pub. Date: Oct. 14, 2021

(65) Prior Publication Data

US 2023/0151110 A1 May 18, 2023

(30) Foreign Application Priority Data

Apr. 10, 2020 (CN) ......................... 202010282924.0

(51) Int. Cl.
*C07K 16/28* (2006.01)
*A61P 35/00* (2006.01)

(52) U.S. Cl.
CPC .......... *C07K 16/2896* (2013.01); *A61P 35/00* (2018.01); *C07K 2317/24* (2013.01); *C07K 2317/565* (2013.01); *C07K 2317/92* (2013.01)

(58) Field of Classification Search
CPC ............ C07K 16/2896; C07K 2317/24; C07K 2317/565; C07K 2317/92; C07K 2317/73; C07K 2317/76; C07K 16/2803; A61P 35/00; A61K 2039/505; A61K 2039/545; G01N 33/564; G01N 33/566
See application file for complete search history.

(56) References Cited

U.S. PATENT DOCUMENTS

| | | | | |
|---|---|---|---|---|
| 9,650,441 | B2 | 5/2017 | Grosveld et al. | |
| 2006/0188508 | A1 * | 8/2006 | Cohen ................ | C07K 14/4747 424/155.1 |
| 2018/0201677 | A1 | 7/2018 | Grosveld et al. | |
| 2020/0181259 | A1 | 6/2020 | Tsun et al. | |
| 2022/0119520 | A1 | 4/2022 | Wang et al. | |

FOREIGN PATENT DOCUMENTS

| | | | |
|---|---|---|---|
| CN | 106117354 | | 11/2016 |
| CN | 107955071 | | 4/2018 |
| CN | 108779179 | A | 11/2018 |
| CN | 110066336 | | 7/2019 |
| CN | 110872350 | A | 3/2020 |
| JP | 2019-537547 | A | 12/2019 |
| JP | 2020-508645 | A | 3/2020 |
| WO | 2011/143624 | A2 | 11/2011 |
| WO | 2011/143624 | A3 | 11/2011 |
| WO | WO 2011/143624 | | 11/2011 |
| WO | 2014/123580 | A1 | 8/2014 |
| WO | 2017/049251 | A2 | 3/2017 |
| WO | 2018/075857 | A1 | 4/2018 |
| WO | 2019/027903 | A1 | 2/2019 |
| WO | WO 2019/042119 | | 3/2019 |
| WO | 2019/144895 | A1 | 8/2019 |
| WO | 2023/056969 | A1 | 4/2023 |
| WO | 2023/056970 | A1 | 4/2023 |
| WO | 2023/056971 | A1 | 4/2023 |

OTHER PUBLICATIONS

McCarthy et al. (J. Immunol. Methods, 251(1-2): 137-149, 2001).*
Lin et al. (African Journal of Biotechnology, 10(79): 18294-18302, 2011).*
Advani, R. et al., "051: The First-in-Class ANTI-CD47 Antibody HU5F9-G4 + Rituximab Induces Durable Responses in Relapsed/Refractory DLBCL and Indolent Lymphoma: Interim Phase 1B/2 Results," Hematological Oncology, Wiley, vol. 37, pp. 89-90, (2019).
Advani, R. et al., "CD47 Blockade by Hu5F9-G4 and Rituximab in Non-Hodgkin's Lymphoma," The New England Journal of Medicine, vol. 379, No. 18, 11 pages, (2018).
Altschuler, E. et al., "Obtaining recombinant antibodies and ways to increase their affinity," Advances in Biological Chemistry, vol. 50, pp. 203-258, (2010), English translation of pp. 203-204.
Altschuler, E. et al., "Obtaining recombinant antibodies and ways to increase their affinity," Advances in Biological Chemistry, vol. 50, pp. 203-258, (2010), in Russian language.
Coico, R., et al., "Immunology: A Short Course" Akademiya, pp. 61-62, (2008), in Russian language.
English Machine Translation of "Coico, R., et al., "Immunology: A Short Course" Akademiya, pp. 61-62, (2008),".
GenBank Accession No. AAB61661.1, retrieved on Feb. 7, 2023 from https://www.ncbi.nlm.nih.gov/protein/AAB61661, 2 pages.
GenBank Accession No. 6IAP_E, retrieved on Feb. 7, 2023 from https://www.ncbi.nlm.nih.gov/protein/6IAP_E, 4 pages.
Sikic, et al., "First-in-Human, First-in-Class Phase I Trial of the Anti-CD47 Antibody Hu5F9-G4 in Patients With Advanced Cancers", Journal of Clinical Oncology, 37(12), pp. 946-953.

(Continued)

*Primary Examiner* — Nelson B Moseley, II
(74) *Attorney, Agent, or Firm* — Hoxie & Associates LLC

(57) ABSTRACT

The present invention provides an anti-CD47 antibody or antigen-binding fragment thereof, a preparation method therefor and the use for treating or preventing CD47-related diseases.

22 Claims, 6 Drawing Sheets

Specification includes a Sequence Listing.

(56) References Cited

OTHER PUBLICATIONS

Liu et al., "Pre-Clinical Development of a Humanized Anti-CD47 Antibody with Anti-Cancer Therapeutic Potential", *PLoS One*, 10(9), e0137345, (2015).

Brown, M. et al., "Tolerance of single, but not multiple, amino acid replacements in antibody VH CDR 2," The Journal of Immunology, vol. 156, No. 9, pp. 3285-3291, (1996).

Chen, C. et al., "Enhancement and destruction of antibody function by somatic mutation: unequal occurrence is controlled by V gene combinatorial associations," The EMBO Journal, vol. 14, No. 12, pp. 2784-2794, 11 pages, (1995).

Colman, P., "Effects of amino acid sequence changes on antibody-antigen interactions," Research in Immunology, vol. 145, No. 1, pp. 33-36, 4 pages, (1994).

Rudikoff, S. et al., "Single amino acid substitution altering antigen-binding specificity," Proc. Natl. Acad. Sci., vol. 79, pp. 1979-1983, 5 pages, (1982).

"Blocking CD47 Shrinks Pancreatic Tumors," Cancer Discovery, p. 864, (2014).

Majeti, R. et al., "CD47 Is an Adverse Prognostic Factor and Therapeutic Antibody Target on Human Acute Myeloid Leukemia Stem Cells," Cell, vol. 138, No. 2, pp. 286-299, (2009).

Zhang, M. et al., "Anti-CD47 Treatment Stimulates Phagocytosis of Glioblastoma by M1 and M2 Polarized Macrophages and Promotes M1 Polarized Macrophages In Vivo," PLoS One, vol. 11, No. 4, e0153550, 21 pages, (2016).

* cited by examiner

SEQUENCE LISTING

```
<160> NUMBER OF SEQ ID NOS: 22

<210> SEQ ID NO 1
<211> LENGTH: 120
<212> TYPE: PRT
<213> ORGANISM: artificial sequence
<220> FEATURE:
<223> OTHER INFORMATION: Synthetic construct

<400> SEQUENCE: 1

Gln Val Gln Leu Gln Gln Ser Gly Thr Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Tyr Met His Trp Val Lys Gln Arg Pro Gly Gln Ile Leu Glu Trp Ile
        35                  40                  45

Gly Tyr Ile Asp Pro Ala Asn Asp Tyr Ser Asp Tyr Asn Gln Asn Phe
    50                  55                  60

Lys Asp Lys Ala Thr Leu Thr Ala Asp Lys Ser Ser Arg Thr Thr Tyr
65                  70                  75                  80

Met Gln Leu Thr Ser Leu Thr Ser Glu Asp Ser Ala Val Tyr Tyr Cys
                85                  90                  95

Ala Arg Leu Gly Tyr Gly Asn Ser Ser Pro Phe Asp Tyr Trp Gly Gln
            100                 105                 110

Gly Thr Thr Leu Ile Val Ser Ser
        115                 120


<210> SEQ ID NO 2
<211> LENGTH: 106
<212> TYPE: PRT
<213> ORGANISM: artificial sequence
<220> FEATURE:
<223> OTHER INFORMATION: Synthetic construct

<400> SEQUENCE: 2

Asp Ile Lys Met Thr Gln Ser Pro Ser Ser Met Tyr Ala Ser Val Gly
1               5                   10                  15

Glu Arg Val Thr Ile Thr Cys Lys Ala Ser Gln Asp Ile His Asn Tyr
            20                  25                  30

Leu Ser Trp Phe Gln Gln Lys Pro Gly Lys Ser Pro Lys Thr Leu Ile
        35                  40                  45

Tyr Arg Ala Lys Arg Leu Val Asp Gly Val Pro Leu Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Phe Cys Leu Gln Tyr Asp Glu Leu Tyr Thr
                85                  90                  95

Phe Gly Gly Gly Thr Arg Leu Glu Ile Lys
            100                 105
```

<210> SEQ ID NO 3
<211> LENGTH: 120
<212> TYPE: PRT
<213> ORGANISM: artificial sequence
<220> FEATURE:
<223> OTHER INFORMATION: Synthetic construct

<400> SEQUENCE: 3

```
Gln Val Gln Leu Gln Gln Ser Gly Thr Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Tyr Met His Trp Val Lys Gln Arg Pro Gly Gln Ile Leu Glu Trp Ile
        35                  40                  45

Gly Tyr Ile Asp Pro Ala Asn Asp Tyr Ser Asp Tyr Asn Gln Asn Phe
    50                  55                  60

Lys Asp Lys Ala Thr Leu Thr Ala Asp Lys Ser Ser Arg Thr Thr Tyr
65                  70                  75                  80

Met Gln Leu Thr Ser Leu Thr Ser Glu Asp Ser Ala Val Tyr Tyr Cys
                85                  90                  95

Ala Arg Leu Gly Tyr Gly Gln Ser Ser Pro Phe Asp Tyr Trp Gly Gln
            100                 105                 110

Gly Thr Thr Leu Ile Val Ser Ser
        115                 120
```

<210> SEQ ID NO 4
<211> LENGTH: 106
<212> TYPE: PRT
<213> ORGANISM: artificial sequence
<220> FEATURE:
<223> OTHER INFORMATION: Synthetic construct

<400> SEQUENCE: 4

```
Asp Ile Lys Met Thr Gln Ser Pro Ser Ser Met Tyr Ala Ser Val Gly
1               5                   10                  15

Glu Arg Val Thr Ile Thr Cys Lys Ala Ser Gln Asp Ile His Asn Tyr
            20                  25                  30

Leu Ser Trp Phe Gln Gln Lys Pro Gly Lys Ser Pro Lys Thr Leu Ile
        35                  40                  45

Tyr Arg Ala Lys Arg Leu Val Glu Gly Val Pro Leu Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Phe Cys Leu Gln Tyr Asp Glu Leu Tyr Thr
                85                  90                  95

Phe Gly Gly Gly Thr Arg Leu Glu Ile Lys
            100                 105
```

<210> SEQ ID NO 5
<211> LENGTH: 120
<212> TYPE: PRT
<213> ORGANISM: artificial sequence
<220> FEATURE:
<223> OTHER INFORMATION: Synthetic construct

<400> SEQUENCE: 5

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30
```

```
Tyr Met His Trp Val Arg Gln Ala Pro Gly Gln Gly Leu Glu Trp Met
        35                  40                  45

Gly Tyr Ile Asp Pro Ala Asn Asp Tyr Ser Asp Tyr Asn Gln Asn Phe
    50                  55                  60

Lys Asp Arg Val Thr Ile Thr Ala Asp Lys Ser Thr Arg Thr Ala Tyr
65                  70                  75                  80

Met Glu Leu Thr Ser Leu Arg Ser Glu Asp Thr Ala Val Tyr Tyr Cys
                85                  90                  95

Ala Arg Leu Gly Tyr Gly Gln Ser Ser Pro Phe Asp Tyr Trp Gly Gln
            100                 105                 110

Gly Thr Thr Val Thr Val Ser Ser
        115                 120


<210> SEQ ID NO 6
<211> LENGTH: 120
<212> TYPE: PRT
<213> ORGANISM: artificial sequence
<220> FEATURE:
<223> OTHER INFORMATION: Synthetic construct

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Tyr Ile Asp Pro Ala Asn Asp Tyr Ser Asp Tyr Asn Gln Asn Phe
    50                  55                  60

Lys Asp Arg Val Thr Ile Thr Ala Asp Lys Ser Thr Arg Thr Thr Tyr
65                  70                  75                  80

Met Glu Leu Thr Ser Leu Arg Ser Glu Asp Thr Ala Val Tyr Tyr Cys
                85                  90                  95

Ala Arg Leu Gly Tyr Gly Gln Ser Ser Pro Phe Asp Tyr Trp Gly Gln
            100                 105                 110

Gly Thr Thr Val Thr Val Ser Ser
        115                 120


<210> SEQ ID NO 7
<211> LENGTH: 120
<212> TYPE: PRT
<213> ORGANISM: artificial sequence
<220> FEATURE:
<223> OTHER INFORMATION: Synthetic construct

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Tyr Ile Asp Pro Ala Asn Asp Tyr Ser Asp Tyr Asn Gln Asn Phe
    50                  55                  60

Lys Asp Arg Ala Thr Leu Thr Ala Asp Lys Ser Thr Arg Thr Thr Tyr
65                  70                  75                  80

Met Glu Leu Thr Ser Leu Arg Ser Glu Asp Thr Ala Val Tyr Tyr Cys
```

```
                85                  90                  95

Ala Arg Leu Gly Tyr Gly Gln Ser Ser Pro Phe Asp Tyr Trp Gly Gln
            100                 105                 110

Gly Thr Thr Val Thr Val Ser Ser
        115                 120


<210> SEQ ID NO 8
<211> LENGTH: 106
<212> TYPE: PRT
<213> ORGANISM: artificial sequence
<220> FEATURE:
<223> OTHER INFORMATION: Synthetic construct

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile His Asn Tyr
            20                  25                  30

Leu Ser Trp Phe Gln Gln Lys Pro Gly Lys Ala Pro Lys Ser Leu Ile
        35                  40                  45

Tyr Arg Ala Lys Arg Leu Val Glu Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Asp Glu Leu Tyr Thr
                85                  90                  95

Phe Gly Gln Gly Thr Arg Leu Glu Ile Lys
            100                 105


<210> SEQ ID NO 9
<211> LENGTH: 106
<212> TYPE: PRT
<213> ORGANISM: artificial sequence
<220> FEATURE:
<223> OTHER INFORMATION: Synthetic construct

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile His Asn Tyr
            20                  25                  30

Leu Ser Trp Phe Gln Gln Lys Pro Gly Lys Ala Pro Lys Ser Leu Ile
        35                  40                  45

Tyr Arg Ala Lys Arg Leu Val Glu Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Leu Tyr Thr
                85                  90                  95

Phe Gly Gln Gly Thr Arg Leu Glu Ile Lys
            100                 105


<210> SEQ ID NO 10
<211> LENGTH: 106
<212> TYPE: PRT
<213> ORGANISM: artificial sequence
<220> FEATURE:
<223> OTHER INFORMATION: Synthetic construct

<400> SEQUENCE: 10
```

```
Asp Ile Lys Met Thr Gln Ser Pro Ser Ser Leu Ser Ala Ser Val Gly
1               5                   10                  15

Asp Arg Val Thr Ile Thr Cys Lys Ala Ser Gln Asp Ile His Asn Tyr
            20                  25                  30

Leu Ser Trp Phe Gln Gln Lys Pro Gly Lys Ala Pro Lys Thr Leu Ile
        35                  40                  45

Tyr Arg Ala Lys Arg Leu Val Glu Gly Val Pro Leu Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Phe Cys Leu Gln Tyr Asp Glu Leu Tyr Thr
                85                  90                  95

Phe Gly Gln Gly Thr Arg Leu Glu Ile Lys
            100                 105


<210> SEQ ID NO 11
<211> LENGTH: 5
<212> TYPE: PRT
<213> ORGANISM: artificial sequence
<220> FEATURE:
<223> OTHER INFORMATION: Synthetic construct

<400> SEQUENCE: 11

Ser Tyr Tyr Met His
1               5


<210> SEQ ID NO 12
<211> LENGTH: 17
<212> TYPE: PRT
<213> ORGANISM: artificial sequence
<220> FEATURE:
<223> OTHER INFORMATION: Synthetic construct

<400> SEQUENCE: 12

Tyr Ile Asp Pro Ala Asn Asp Tyr Ser Asp Tyr Asn Gln Asn Phe Lys
1               5                   10                  15

Asp


<210> SEQ ID NO 13
<211> LENGTH: 11
<212> TYPE: PRT
<213> ORGANISM: artificial sequence
<220> FEATURE:
<223> OTHER INFORMATION: Synthetic construct

<400> SEQUENCE: 13

Leu Gly Tyr Gly Asn Ser Ser Pro Phe Asp Tyr
1               5                   10


<210> SEQ ID NO 14
<211> LENGTH: 11
<212> TYPE: PRT
<213> ORGANISM: artificial sequence
<220> FEATURE:
<223> OTHER INFORMATION: Synthetic construct

<400> SEQUENCE: 14

Lys Ala Ser Gln Asp Ile His Asn Tyr Leu Ser
1               5                   10


<210> SEQ ID NO 15
<211> LENGTH: 7
```

<212> TYPE: PRT
<213> ORGANISM: artificial sequence
<220> FEATURE:
<223> OTHER INFORMATION: Synthetic construct

<400> SEQUENCE: 15

Arg Ala Lys Arg Leu Val Asp
1               5

<210> SEQ ID NO 16
<211> LENGTH: 8
<212> TYPE: PRT
<213> ORGANISM: artificial sequence
<220> FEATURE:
<223> OTHER INFORMATION: Synthetic construct

<400> SEQUENCE: 16

Leu Gln Tyr Asp Glu Leu Tyr Thr
1               5

<210> SEQ ID NO 17
<211> LENGTH: 11
<212> TYPE: PRT
<213> ORGANISM: artificial sequence
<220> FEATURE:
<223> OTHER INFORMATION: Synthetic construct

<400> SEQUENCE: 17

Leu Gly Tyr Gly Gln Ser Ser Pro Phe Asp Tyr
1               5                   10

<210> SEQ ID NO 18
<211> LENGTH: 7
<212> TYPE: PRT
<213> ORGANISM: artificial sequence
<220> FEATURE:
<223> OTHER INFORMATION: Synthetic construct

<400> SEQUENCE: 18

Arg Ala Lys Arg Leu Val Glu
1               5

<210> SEQ ID NO 19
<211> LENGTH: 360
<212> TYPE: DNA
<213> ORGANISM: artificial sequence
<220> FEATURE:
<223> OTHER INFORMATION: Synthetic construct

<400> SEQUENCE: 19
caggtccagc ttcagcagtc tgggactgaa ctggcaaaac ccggggcctc agtgaagatg     60
tcctgcaagg cttctgggta cacgtttact agttattata tgcactgggt aaaacagagg    120
cctggacaaa ttctggagtg gattggatac attgatcctg ccaatgatta tagtgactac    180
aatcagaatt tcaaggacaa ggccacattg actgcagaca aatcctccag gacaacctac    240
atgcaactga ccagcctgac atctgaggac tctgcagtct attattgtgc aagattgggc    300
tacggtaata gctccccttt tgactactgg ggccaaggca ccactctcat agtatcttca    360

<210> SEQ ID NO 20
<211> LENGTH: 318
<212> TYPE: DNA
<213> ORGANISM: artificial sequence
<220> FEATURE:
<223> OTHER INFORMATION: Synthetic construct -continued

```
<400> SEQUENCE: 20

gacatcaaga tgacccagtc tccatcttcc atgtatgcat ctgtaggaga gagagtcact     60

atcacttgca aggcgagtca ggacattcat aactatttaa gttggttcca gcagaaacca    120

gggaaatctc ctaagaccct gatctatcgt gcaaaaagat tggtagatgg ggtcccatta    180

aggttcagtg gcagtggatc tgggcaagat tattctctca ccatcagcag cctggagtat    240

gaagatatgg gaatttattt ttgtctacag tatgatgagt tgtacacgtt cggagggggg    300

accaggctgg aaataaaa                                                  318


<210> SEQ ID NO 21
<211> LENGTH: 11
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (5)..(5)
<223> OTHER INFORMATION: Xaa can be any naturally occurring amino acid,
      preferably N or Q or H, D, K, R or E, or a conservative amino acid
      thereof

<400> SEQUENCE: 21

Leu Gly Tyr Gly Xaa Ser Ser Pro Phe Asp Tyr
1               5                   10


<210> SEQ ID NO 22
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (7)..(7)
<223> OTHER INFORMATION: Xaa can be any naturally occurring amino acid,
      preferably D or E or N or Q, or a conservative amino acid thereof

<400> SEQUENCE: 22

Arg Ala Lys Arg Leu Val Xaa
1               5
```

ANTI-CD47 ANTIBODY AND USES THEREOF

CROSS REFERENCE TO RELATED APPLICATIONS

This application is a United States Application under 35 U.S.C. § 371 claiming priority to, and the benefit of, International Application No. PCT/CN2021/086339, filed on Apr. 11, 2021, which is based on and claims priority to Chinese patent application No. CN202010282924.0, which is filed on Apr. 10, 2020 and is entirely incorporated herein by reference for all purposes.

This application is based on and claims priority to CN202010282924.0, which is filed on Apr. 10, 2020 and is entirely incorporated herein by reference for all purposes.

TECHNICAL FIELD

The present invention relates to an antibody, and in particular to an anti-CD47 antibody and the use thereof for preparing a drug for treating or preventing CD47-related diseases.

BACKGROUND ART

CD47 (Cluster of Differentiation 47) was firstly identified as the tumor antigen of human ovarian cancer in 1980s. CD47, also known as an integrin-associated protein (IAP), ovarian cancer antigen OA3, Rh-related antigen and MER6, is a multiple membrane receptor belonging to an immunoglobulin superfamily that has a single immunoglobulin-like domain and five membrane spanning regions. As a ligand of signal regulatory protein α (SIRPα), CD47 binds to the V-like domain at the $NH_2$ terminus of SIRPα. SIRPα is expressed primarily on bone marrow cells, including macrophages, granulocytes, dendritic cells (DCs), mast cells and their precursors, e.g. hematopoietic stem cells. CD47 on normal cells binds to SIRPα on macrophages, which releases the "don't eat me" signal, and thereby inhibits the phagocytic function of macrophages. It is an important mechanism how macrophages distinguish self from non-self in the innate immune system. CD47 is widely expressed on human tumor cells and tissues, including acute myelogenous leukemia (AML), chronic granulocytic leukemia, acute lymphocytic leukemia (ALL), non-Hodgkin's lymphoma (NHL), multiple myeloma (MM), bladder cancer and other solid tumors. The tumor cells escape from the phagocytosis of macrophages though the binding of highly expressed CD47 to SIRPα on the surface of macrophages, which favors tumor growth. The immune checkpoint CD47 is considered to be a target which is potentially effective and can be widely used for tumor immunotherapy. At present, a variety of specific blockers have been developed to target the CD47/SIRPα interaction. There are a number of preclinical and clinical trials being carried out, which relates to the drugs including anti-CD47 antibodies and SIRPα fusion proteins for treatment in diffuse large B cell lymphoma, acute myelogenous leukemia, and advanced solid tumors. These drugs are administered either alone or in combination with other anti-tumor drugs. Taking the anti-CD47 antibody Hu5F9 developed by Forty Seven company as an example, in a phase I clinical trial to evaluate the effect of Hu5F9 in the treatment of 22 patients with lymphoma, the combination of Hu5F9 and Rituximab could produce objective remission in 50% of patients who did not respond to Rituximab alone. According to the clinical data published in 2019, the complete remission rate of 14 patients with recurrent/refractory acute myelogenous leukemia treated with Hu5F9 in combination with Azacitidine is up to 36%, and the remission rate of 11 patients with bone marrow suppression syndrome treated with Hu5F9 in combination with Azacitidine is up to 55%.

The present invention provides a novel anti-CD47 antibody or antigen-binding fragment thereof, which has a high anti-tumor activity and does not cause a significant agglutination of red blood cells. So the present invention can satisfy more clinical demands.

SUMMARY OF THE INVENTION

The present invention provides an anti-CD47 antibody or antigen-binding fragment thereof, which binds to CD47 or a fragment thereof, and a method for preparing and using same, including a method for treating CD47-related diseases.

In one aspect, the present invention provides an anti-CD47 antibody or antigen-binding fragment thereof, comprising one to three selected from HCDR1, HCDR2 and HCDR3 of a heavy chain variable region (VH), wherein the amino acid sequence of the VH is as set forth in SEQ ID NO: 1, 3, 5, 6 or 7.

In one aspect, the anti-CD47 antibody or antigen-binding fragment thereof provided by the present invention comprises one to three selected from heavy chain complementary determining region 1 (HCDR1), HCDR2 and HCDR3, wherein the HCDR1 comprises the amino acid sequence as set forth in SEQ ID NO: 11, the HCDR2 comprises the amino acid sequence as set forth in SEQ ID NO: 12, and the HCDR3 comprises the amino acid sequence as set forth in SEQ ID NO: 13 or 17 or 21.

In one aspect, the present invention provides an anti-CD47 antibody or antigen-binding fragment thereof, comprising one to three selected from LCDR1, LCDR2 and LCDR3 of a light chain variable region (VL), wherein the amino acid sequence of the VL is as set forth in SEQ ID NO: 2, 4, 8, 9 or 10.

In one aspect, the present invention provides an anti-CD47 antibody or antigen-binding fragment thereof, comprising one to three selected from light chain complementary determining region 1 (LCDR1), LCDR2 and LCDR3, wherein the LCDR1 comprises the amino acid sequence as set forth in SEQ ID NO: 14, the LCDR2 comprises the amino acid sequence as set forth in SEQ ID NO: 15 or 18 or 22, and the LCDR3 comprises the amino acid sequence as set forth in SEQ ID NO: 16.

In some embodiments, the present invention provides an CD47 antibody or antigen-binding fragment thereof, which comprises three CDRs of a heavy chain variable region (VH), i.e., HCDR1, HCDR2 and HCDR3, and three CDRs of a light chain variable region (VL), i.e., LCDR1, LCDR2 and LCDR3, wherein the amino acid sequence of the VH is as set forth in SEQ ID NO: 1, 3, 5, 6 or 7, and the amino acid sequence of the VL is as set forth in SEQ ID NO: 2, 4, 8, 9 or 10.

In some embodiments, the present invention provides an anti-CD47 antibody or antigen-binding fragment thereof, which comprises three CDRs of a heavy chain variable region (VH), i.e., HCDR1, HCDR2 and HCDR3, and three CDRs of a light chain variable region (VL), i.e., LCDR1, LCDR2 and LCDR3; wherein the VH and VL are selected from:

(1) a VH comprising the amino acid sequence as set forth in SEQ ID NO: 1, and a VL comprising the amino acid sequence as set forth in SEQ ID NO: 2;

(2) a VH comprising the amino acid sequence as set forth in SEQ ID NO: 3, and a VL comprising the amino acid sequence as set forth in SEQ ID NO: 4;

(3) a VH comprising the amino acid sequence as set forth in SEQ ID NO: 5, and a VL comprising the amino acid sequence as set forth in SEQ ID NO: 8, 9 or 10;

(4) a VH comprising the amino acid sequence as set forth in SEQ ID NO: 6, and a VL comprising the amino acid sequence as set forth in SEQ ID NO: 9 or 10; or (5) a VH comprising the amino acid sequence as set forth in SEQ ID NO: 7, and a VL comprising the amino acid sequence as set forth in SEQ ID NO: 8, 9 or 10.

In some embodiments, the present invention provides an anti-CD47 antibody or antigen-binding fragment thereof, comprising heavy chain complementary determining region 1 (HCDR1), HCDR2 and HCDR3, and light chain complementary determining region 1 (LCDR1), LCDR2 and LCDR3, wherein the HCDR1 comprises the amino acid sequence as set forth in SEQ ID NO: 11, the HCDR2 comprises the amino acid sequence as set forth in SEQ ID NO: 12, the HCDR3 comprises the amino acid sequence as set forth in SEQ ID NO: 13 or 17 or 21, the LCDR1 comprises the amino acid sequence as set forth in SEQ ID NO: 14, the LCDR2 comprises the amino acid sequence as set forth in SEQ ID NO: 15 or 18 or 22, and the LCDR3 comprises the amino acid sequence as set forth in SEQ ID NO: 16.

In some embodiments, the anti-CD47 antibody or antigen-binding fragment thereof provided by the present invention comprises heavy chain complementary determining region 1(HCDR1), HCDR2 and HCDR3, and light chain complementary determining region 1(LCDR1), LCDR2 and LCDR3, wherein the HCDR1 comprises the amino acid sequence as set forth in SEQ ID NO: 11, the HCDR2 comprises the amino acid sequence as set forth in SEQ ID NO: 12, the HCDR3 comprises the amino acid sequence as set forth in SEQ ID NO: 17, the LCDR1 comprises the amino acid sequence as set forth in SEQ ID NO: 14, the LCDR2 comprises the amino acid sequence as set forth in SEQ ID NO: 18, and the LCDR3 comprises the amino acid sequence of SEQ ID NO: 16.

In some embodiments, the anti-CD47 antibody or antigen-binding fragment thereof provided by the present invention comprises a heavy chain variable region (VH), wherein the VH comprises an amino acid sequence identical to or having at least 90%, 91%, 92%, 93%, 94%, 95%, 96%, 97%, 98% or 99% sequence identity to the amino acid sequence as set forth in SEQ ID NO: 1, 3, 5, 6 or 7.

In some embodiments, the anti-CD47 antibody or antigen-binding fragment thereof provided by the present invention comprises a light chain variable region (VL), wherein the VL comprises an amino acid sequence identical to or having at least 90%, 91%, 92%, 93%, 94%, 95%, 96%, 97%, 98% or 99% sequence identity to the amino acid sequence as set forth in SEQ ID NO: 2, 4, 8, 9 or 10.

In some embodiments, the anti-CD47 antibody or antigen-binding fragment thereof provided by the present invention comprises a heavy chain variable region (VH) and a light chain variable region (VL), wherein the VH comprises an amino acid sequence identical to or having at least 90%, 91%, 92%, 93%, 94%, 95%, 96%, 97%, 98% or 99% sequence identity to the amino acid sequence as set forth in SEQ ID NO: 1, 3, 5, 6 or 7, wherein the VL comprises an amino acid sequence identical to or having at least 90%, 91%, 92%, 93%, 94%, 95%, 96%, 97%, 98% or 99% sequence identity to the amino acid sequence as set forth in SEQ ID NO: 2, 4, 8, 9 or 10.

In some embodiments, the anti-CD47 antibody or antigen-binding fragment thereof provided by the present invention comprises a heavy chain variable region (VH) and a light chain variable region (VL), wherein the VH comprises an amino acid sequence identical to or having at least 90%, 91%, 92%, 93%, 94%, 95%, 96%, 97%, 98% or 99% sequence identity to the amino acid sequence as set forth in SEQ ID NO: 7, wherein the VL comprises an amino acid sequence identical to or having at least 90%, 91%, 92%, 93%, 94%, 95%, 96%, 97%, 98% or 99% sequence identity to the amino acid sequence as set forth in SEQ ID NO: 8.

In some embodiments, the anti-CD47 antibody or antigen-binding fragment thereof provided by the present invention comprises a heavy chain variable region (VH) and a light chain variable region (VL), wherein the VH and VL are selected from (1) a VH comprising the amino acid sequence as set forth in SEQ ID NO: 1, and a VL comprising the amino acid sequence as set forth in SEQ ID NO: 2;

(2) a VH comprising the amino acid sequence as set forth in SEQ ID NO: 3, and a VL comprising the amino acid sequence as set forth in SEQ ID NO: 4;

(3) a VH comprising the amino acid sequence as set forth in SEQ ID NO: 5, and a VL comprising the amino acid sequence as set forth in SEQ ID NO: 8, 9 or 10;

(4) a VH comprising the amino acid sequence as set forth in SEQ ID NO: 6, and a VL comprising the amino acid sequence as set forth in SEQ ID NO: 9 or 10; or (5) a VH comprising the amino acid sequence as set forth in SEQ ID NO: 7, and a VL comprising the amino acid sequence as set forth in SEQ ID NO: 8, 9 or 10.

In some embodiments, the anti-CD47 antibody or antigen-binding fragment thereof provided by the present invention comprises a heavy chain variable region (VH) and a light chain variable region (VL), wherein the VH comprises the amino acid sequence as set forth in SEQ ID NO: 1, and wherein the VL comprises the amino acid sequence as set forth in SEQ ID NO: 2.

In some embodiments, the anti-CD47 antibody or antigen-binding fragment thereof provided by the present invention comprises a heavy chain variable region (VH) and a light chain variable region (VL), wherein the VH comprises the amino acid sequence as set forth in SEQ ID NO: 3, and wherein the VL comprises the amino acid sequence as set forth in SEQ ID NO: 4.

In some embodiments, the anti-CD47 antibody or antigen-binding fragment thereof provided by the present invention comprises a heavy chain variable region (VH) and a light chain variable region (VL), wherein the VH comprises the amino acid sequence as set forth in SEQ ID NO: 5, and wherein the VL comprises the amino acid sequence as set forth in SEQ ID NO: 8.

In some embodiments, the anti-CD47 antibody or antigen-binding fragment thereof provided by the present invention comprises a heavy chain variable region (VH) and a light chain variable region (VL), wherein the VH comprises the amino acid sequence as set forth in SEQ ID NO: 5, and wherein the VL comprises the amino acid sequence as set forth in SEQ ID NO: 9.

In some embodiments, the anti-CD47 antibody or antigen-binding fragment thereof provided by the present invention comprises a heavy chain variable region (VH) and a light chain variable region (VL), wherein the VH comprises the amino acid sequence as set forth in SEQ ID NO: 5, and wherein the VL comprises the amino acid sequence as set forth in SEQ ID NO: 10.

In some embodiments, the anti-CD47 antibody or antigen-binding fragment thereof provided by the present invention comprises a heavy chain variable region (VH) and a light chain variable region (VL), wherein the VH comprises the amino acid sequence as set forth in SEQ ID NO: 6, and wherein the VL comprises the amino acid sequence as set forth in SEQ ID NO: 9.

In some embodiments, the anti-CD47 antibody or antigen-binding fragment thereof provided by the present invention comprises a heavy chain variable region (VH) and a light chain variable region (VL), wherein the VH comprises the amino acid sequence as set forth in SEQ ID NO: 6, and wherein the VL comprises the amino acid sequence as set forth in SEQ ID NO: 10.

In some embodiments, the anti-CD47 antibody or antigen-binding fragment thereof provided by the present invention comprises a heavy chain variable region (VH) and a light chain variable region (VL), wherein the VH comprises the amino acid sequence as set forth in SEQ ID NO: 7, and wherein the VL comprises the amino acid sequence as set forth in SEQ ID NO: 8.

In some embodiments, the anti-CD47 antibody or antigen-binding fragment thereof provided by the present invention comprises a heavy chain variable region (VH) and a light chain variable region (VL), wherein the VH comprises the amino acid sequence as set forth in SEQ ID NO: 7, and wherein the VL comprises the amino acid sequence as set forth in SEQ ID NO: 9.

In some embodiments, the anti-CD47 antibody or antigen-binding fragment thereof provided by the present invention comprises a heavy chain variable region (VH) and a light chain variable region (VL), wherein the VH comprises the amino acid sequence as set forth in SEQ ID NO: 7, and wherein the VL comprises the amino acid sequence as set forth in SEQ ID NO: 10.

In some embodiments, the anti-CD47 antibody or antigen-binding fragment thereof provided by the present invention comprises a heavy chain constant region, wherein the heavy chain constant region is, for example, a human IgG1 constant region, a human IgG4 constant region, a human IgG4P constant region or a human IgG1TM constant region. The human IgG4P constant region of the present invention is a mutant human IgG4, which has an amino acid substitution of S228P (numbered according to EU). In some embodiments, the human IgG1TM constant region is a mutant human IgG1 constant region, which has amino acid substitutions of L234F, L235E and P331S (numbered according to EU).

In some embodiments, the anti-CD47 antibody or antigen-binding fragment thereof provided by the present invention comprises a light chain constant region, such as a human κ or λ constant region.

In some embodiments, the anti-CD47 antibody or antigen-binding fragment thereof provided by the present invention is a monoclonal antibody. In some embodiments, the anti-CD47 antibody or antigen-binding fragment thereof provided by the present invention is a murine antibody, a chimeric antibody or a humanized antibody. In some embodiments, at least part of the framework sequence of the anti-CD47 antibody or antigen-binding fragment thereof provided by the present invention is a human consensus framework sequence. In one embodiment, the anti-CD47 antibody or antigen-binding fragment thereof provided by the present invention is a full-length antibody, a single-domain antibody such as a VHH, a Fab, a Fab', a Fab'-SH, a $(Fab')_2$, a single-chain antibody such as a scFv, a Fv, a dAb (domain antibody) or a bis (multi)-specific antibody.

In another aspect, the present invention provides an isolated nucleic acid, which encodes any anti-CD47 antibody or antigen-binding fragment thereof provided by the present invention, wherein preferably, the nucleic acid encodes the heavy chain or the light chain, or the heavy chain variable region or the light chain variable region of the antibody of the present invention.

In another aspect, the present invention provides a recombinant vector or expression vector, comprising one or more nucleic acids provided by the present invention, wherein the vector is suitable for recombinant production of any antibody or antigen-binding fragment thereof provided by the present invention. In some embodiments, the vector is an expression vector.

In another aspect, the present invention provides a host cell, comprising one or more nucleic acids, or recombinant vectors or expression vectors provided by the present invention.

In another aspect, the present invention provides an immunoconjugate or immune fusion, comprising the anti-CD47 antibody or antigen-binding fragment thereof provided by the present invention.

In another aspect, the present invention provides a pharmaceutical composition, comprising the anti-CD47 antibody or antigen-binding fragment thereof provided by the present invention, the nucleic acid, vector or host cell provided by the present invention, and optionally comprising at least one pharmaceutically acceptable pharmaceutical excipient, such as a carrier or excipient.

In another aspect, the present invention provides a method for treating or preventing CD47-related diseases, which method comprises administering to a subject an effective amount of any antibody or antigen-binding fragment thereof described herein, the nucleic acid, vector or host cell provided by the present invention, the immunoconjugate or immune fusion provided by the present invention, or the pharmaceutical composition provided by the present invention.

In another aspect, the present invention also provides the use of the anti-CD47 antibody or antigen-binding fragment thereof of the present invention in the preparation of drugs for treating or preventing CD47-related diseases.

In some embodiments, the CD47-related diseases include various hematological cancers and solid tumors, including but not limited to bladder cancer, colorectal cancer, pancreatic cancer, lymphomas, leukemia, multiple myeloma, (malignant) melanoma, liomyoma, leiomyosarcomas, glioma, glioblastoma, myeloma, endometrial cancer, renal carcinoma, (benign) melanoma, prostate cancer, thyroid carcinoma, cervical cancer, gastric cancer, and liver cancer.

The CD47 antibody or antigen-binding fragment thereof of the present invention can also be combined with other therapeutic agents or therapeutic modes, for treating or preventing CD47-related diseases.

In some embodiments, the antibody or antigen-binding fragment thereof of the present invention can be used for the detection of CD47 protein in a sample, or for the diagnosis/detection of CD47-related diseases.

The present invention also encompasses any combinations of any embodiments described herein. Any embodiments or any combinations thereof described herein are applicable to any and all anti-CD47 antibodies or fragments, methods and uses thereof of the present invention described herein.

DETAILED DESCRIPTION OF THE INVENTION

Figure 1:
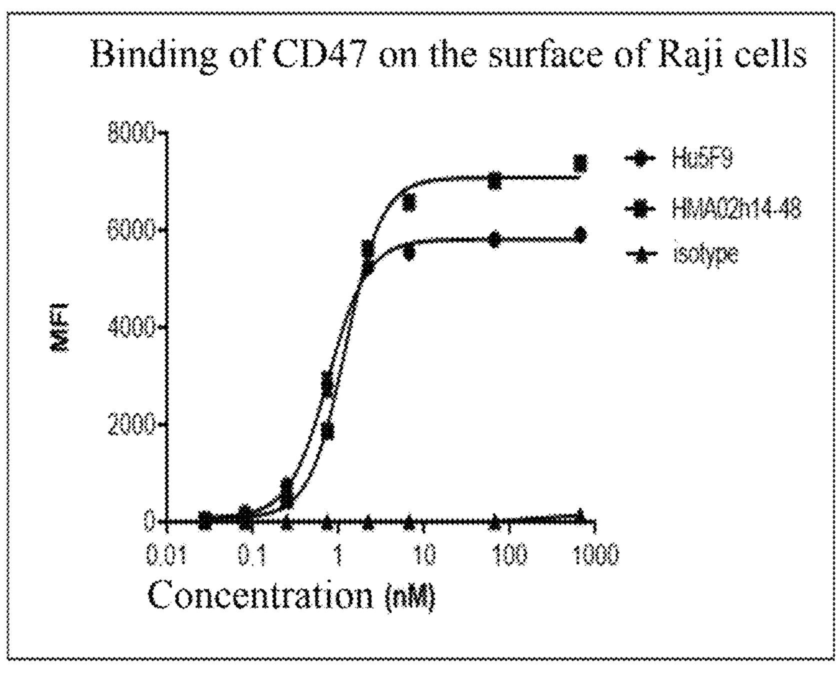
FIG. 1 shows the binding activity of antibody HMA02h14-48 to CD47 on the surface of Raji cells.

The present invention provides an anti-CD47 antibody or antigen-binding fragment thereof, which can block the interaction between CD47 and SIRPα, has a high anti-tumor activity, and does not induce a significant red blood cell agglutination reaction.

The anti-CD47 antibody or antigen-binding fragment thereof provided by the present invention shows an inhibitory activity, such as in inhibiting the expression of CD47 (such as inhibiting the CD47 expression on a cell surface), activity and/or signal transduction of CD47, or blocking the interaction between CD47 and SIRPα. The CD47 antibody provided by the present invention completely or partially reduces or regulates the expression or activity of CD47 after binding to or interacting with CD47 (such as human CD47). After the interaction between the antibody and a human CD47 polypeptide and/or peptide, the biological function of CD47 is completely, significantly or partially decreased or regulated. Compared with the level of CD47 expression or activity without interaction with (e.g., binding to) the anti-CD47 antibody described herein, the level of CD47 expression or activity in the presence of the anti-CD47 antibody is reduced by at least 95% (e.g., reduced by 96%, 97%, 98%, 99% or 100%), and in this case the antibody is thought to be capable of completely inhibiting the expression or activity of CD47. Compared with the level of CD47 expression or activity without interaction with (e.g., binding to) the anti-CD47 antibody described herein, the level of CD47 expression or activity in the presence of the anti-CD47 antibody is reduced by at least 50% (e.g., reduced by 55%, 60%, 75%, 80%, 85% or 90%), and in this case, the CD47 antibody is thought to be capable of significantly inhibiting the expression or activity of CD47. Compared with the level of CD47 expression or activity without interaction with (e.g., binding to) the anti-CD47 antibody described herein, the level of CD47 expression or activity in the presence of the anti-CD47 antibody is reduced by less than 95% (e.g., reduced by 10%, 20%, 25%, 30%, 40%, 50%, 60%, 75%, 80%, 85% or 90%), and in this case, the antibody is thought to be capable of partially inhibiting the expression or activity of CD47.

Comparing the level of interaction between CD47 and SIRPα in presence of the anti-CD47 antibody or the antigen-binding fragment thereof provided by the present invention with the level of interaction between CD47 and SIRPα in the absence of the anti-CD47 antibody or the antigen-binding fragment thereof described herein, the anti-CD47 antibody or the antigen-binding fragment thereof of the present invention blocks the interaction between CD47 and SIRPα by at least 40%, at least 45%, at least 50%, at least 55%, at least 60%, at least 65%, at least 70%, at least 75%, at least 80%, at least 85%, at least 95% or at least 99%.

The anti-CD47 antibody or antigen-binding fragment thereof of the present invention does not induce a significant level of cell agglutination, for example, the CD47 antibody of the present invention does not induce a significant level of red blood cell agglutination. In some embodiments, if the level of red blood cell agglutination in the presence of the CD47 antibody of the present invention is reduced by at least 5%, at least 10%, at least 20%, at least 30%, at least 40%, at least 50%, at least 60%, at least 70%, at least 80%, at least 90% or at least 99% compared with the level of red blood cell agglutination in the presence of the CD47 antibody Hu5F9 in the prior art, it indicates that the CD47 antibody of the present invention does not induce a significant level of red blood cell agglutination.

Compared with the antibody known in the art, the antibody provided by the present invention is also significantly effective in tumor model. In some embodiments, the antibody provided by the present invention can significantly inhibit tumor growth. In some embodiments, the tumor volume in the presence of the antibody of the present invention is inhibited by at least 5%, at least 10%, at least 20%, at least 30%, at least 40%, at least 50%, at least 60%, at least 70%, at least 80%, at least 90%, or at least 99%, or 100%, compared with that in the absence of the antibody. For example, the ability of macrophages to phagocytose tumor cells in the presence of the CD47 antibody of the present invention is increased by at least 5%, at least 10%, at least 20%, at least 30%, at least 40%, at least 50%, at least 60%, at least 70%, at least 80%, at least 90% or at least 99%, compared with that in the presence of the CD47 antibody in the prior art.

The present invention also provides a method for preparing the anti-CD47 antibody or antigen-binding fragment thereof, and the use of the antibody or antigen-binding fragment thereof for treating or preventing cancers, etc.

DEFINITIONS

Unless otherwise stated, the present invention will be implemented using conventional techniques in molecular biology (including recombinant techniques), microbiology, cell biology, biochemistry and immunology, which are within the technical scope in the art.

In order that the invention may be more readily understood, some of the scientific and technical terms are defined as follows. Unless otherwise explicitly defined elsewhere herein, all scientific and technical terms used herein have the meanings generally understood by those of ordinary skill in the art to which the present invention belongs. With respect to definitions and terms in the art, reference can be made to Current Protocols in Molecular Biology (Ausubel) by professionals. The abbreviation of an amino acid residue is a standard 3-letter and/or 1-letter code used in the art to refer to one of the 20 commonly used L-amino acids. The singular form used herein (including the claims) includes the corresponding plural form thereof, unless otherwise explicitly specified.

The term "about" means a value or composition within an acceptable error range of the particular value or composition as determined by one of ordinary skill in the art, which depends in part on how the value or composition is measured or determined, i.e., the limitations of the measurement system. For example, "about" can refer to a scope within 1 or more than 1 standard deviations according to practices in the art. Alternatively, "about" can refer to a range of up to 5%, 10% or 20% (i.e., ±5%, ±10% or ±20%).

When used to connect two or more optional items, the term "and/or" should be understood to mean any one of the optional items or any two or more of the optional items.

As used herein, the term "comprise" or "include" means to include the mentioned elements, integers, or steps, but does not exclude any other elements, integers, or steps. As used herein, when the term "comprise" or "include" is used, unless otherwise indicated, it also encompasses instances composed of the mentioned elements, integers or steps. For example, when referring to an antibody variable region "comprising" a specific sequence, it is also intended to encompass an antibody variable region composed of the specific sequence.

The terms "integrin-associated protein (IAP)" or "CD47", when used herein, refers to any natural CD47 from any vertebrate source, including mammals (such as primates (e.g., humans) and rodents (e.g., mice and rats)), unless otherwise stated. The term covers a "full length" unprocessed CD47 and any form of CD47 or any fragment thereof produced by intracellular processing. The term also includes naturally occurring variants of CD47, such as splice variants or allelic variants. In some embodiments, CD47 refers to a full length CD47 or fragment thereof (such as a mature fragment thereof lacking a signal peptide) from a human. In some embodiments, a human CD47 refers to CD47 identical to the amino acid sequence as set forth in NCBI accession number NP_001768.1 or a fragment thereof. In some embodiments, the term also covers a fusion protein comprising CD47 or a fragment thereof.

"SIRPα" means a wild-type signal regulatory protein α, or recombinant or non-recombinant polypeptide comprising amino acid sequence of wild-type signal regulatory protein α, or a natural or naturally occurring allelic variant of signal regulatory protein α.

The term "anti-CD47 antibody", "anti-CD47", "CD47 antibody" or "an antibody that binds to CD47" refers to an antibody or antigen-binding fragment thereof which is capable of binding to a CD47 protein or fragment thereof with sufficient affinity such that the antibody is useful as a diagnostic and/or therapeutic agent for targeting CD47. In some embodiments, the anti-CD47 antibody provided herein has a dissociation constant (KD) of ≤100 nM, ≤10 nM, ≤5 nM, ≤4 nM, ≤3 nM, ≤2 nM, ≤1 nM, ≤0.9 nM or ≤0.8 nM. In some embodiments, the antibody or antigen-binding fragment thereof binds to a full-length human CD47 or fragment thereof (especially an extracellular binding fragment thereof). In some embodiments, the antibody or antigen-binding fragment thereof binds to a protein comprising a full-length CD47 or fragment thereof. In some other embodiments, the antibody or antigen-binding fragment thereof binds to CD47 or a fragment thereof expressed on a cell surface.

The term "affinity" as used herein refers to the strength of the sum total of all the noncovalent interactions between a single binding site of a molecule (e.g., an antibody) and its binding partner (e.g., an antigen). Unless otherwise indicated, as used herein, "binding affinity" refers to an intrinsic binding affinity which reflects a 1:1 interaction between members of a binding pair (e.g., an antibody and an antigen). The affinity of a molecule X for its partner Y can generally be expressed by the dissociation constant ($K_D$). Examples of analyses known in the art for determining binding affinity include surface plasmon resonance (e.g., BIACORE) or similar techniques (e.g., ForteBio).

The term "CD47-related disease" as used herein refers to a non-physiological state related to the expression or function or activity of CD47, or to the activity of the signal transduction mediated by CD47, including but not limited to cancers. In some embodiments, the diseases will benefit from the blocking of a CD47-related signal transduction.

The term "immune response" or "immune reaction" can be used interchangeably herein and refers to the effect of, such as lymphocytes, antigen presenting cells, phagocytes, granulocytes, and the effects of said cells or liver to produce soluble macromolecules (including antibodies, cytokines and complements). The effect results in the selective impairment, destruction or elimination of invasive pathogens, cells or tissues infected with pathogens, cancer cells, or normal human cells or tissues in the case of autoimmunity or pathological inflammation from the human body.

The term "signal transduction" as used herein refers to a biochemical causal relationship generally initiated by protein-protein interactions such as the binding of CD47 to its receptor, which relationship leads to the transmission of signals from one part of the cell to another part of the cell. Generally, transmission includes the specific phosphorylation of one or more tyrosine, serine, or threonine residues on one or more proteins in a series of reactions that cause the signal transduction. The penultimate process generally includes nuclear events, thereby causing changes in gene expression.

The terms "activity" and "biological activity" or the terms "biological property" and "biological feature" as used herein are used interchangeably herein and include, but are not limited to, epitope/antigen affinity and specificity, the ability to neutralize or antagonize CD47 activity in vivo or in vitro, enhancement or activation of CD47 activity, $IC_{50}$, in vivo stability of an antibody and immunogenicity of an antibody. Other identifiable biological properties or features of antibodies known in the art include, for example, cross reactivity (i.e., cross reactivity, generally with non-human homologs of targeted peptides, or with other proteins or tissues), and the ability to maintain high levels of antibody expression in mammalian cells. The properties or features mentioned above can be observed, determined or evaluated using techniques well known in the art, including but not limited to ELISA, FACS or BIACORE plasmon resonance assay, in vitro or in vivo neutralization assay, receptor binding, production and/or secretion of cytokines or growth factors, signal transduction and immunohistochemistry of tissue sections from different sources (including humans, primates, or any other sources).

The term "antibody" as used herein refers to any form of antibody having a desirable bioactivity. Therefore, it is used in the broadest sense, including but not limited to a monoclonal antibody (including a full-length monoclonal antibody), a polyclonal antibody, a multispecific antibody (such as a bispecific antibody), a humanized antibody, a human antibody, a chimeric antibody, a CrossMab antibody, or a camelized single-domain antibody.

The terms "whole antibody", "full-length antibody", and "intact antibody" are used interchangeably herein and refer to a glycoprotein comprising at least two heavy chains (H) and two light chains (L) interconnected by disulfide bonds. Each heavy chain consists of a heavy chain variable region (hereinafter abbreviated as VH) and a heavy chain constant region. The heavy chain constant region consists of 3 domains CH1, CH2 and CH3. Each light chain consists of a light chain variable region (hereinafter abbreviated as VL) and a light chain constant region. The light chain constant region consists of one domain CL. The VH region and VL region can be further divided into a hypervariable region (being a complementary determining region (CDR)), among which a more conservative region (being a framework region (FR)) is interspersed. A "complementary determining region" or "CDR region" or "CDR" is a region in an antibody variable domain, which is hypervariable in sequence and forms a structurally established loop ("hypervariable loop") and/or contains an antigen contact residue ("antigen contact point"). CDR is mainly responsible for binding to antigen epitopes. CDRs of heavy chain and light chain are generally called CDR1, CDR2 and CDR3, which are numbered sequentially from the N-terminus. The CDRs located in an antibody heavy chain variable domain are called HCDR1, HCDR2 and HCDR3 respectively, while the CDRs located in the antibody light chain variable domain are called LCDR1, LCDR2 and LCDR3 respectively. Each VH or VL consists of three CDRs and 4 FRs, which are arranged in the following order from the amino terminus to the carboxyl terminus: FR1, CDR1, FR2, CDR2, FR3, CDR3, and FR4. The constant region is not directly involved in the binding of an antibody to an antigen, but shows multiple effector functions.

In a given VH or VL amino acid sequence, the accurate amino acid sequence boundary of each CDR can be determined by using any one of the various well known schemes or a combination thereof, including, for example: Chothia scheme (Chothia et al., Canonical Structures for the Hypervariable Regions of Immunoglobulins", Journal of Molecular Biology, 196, 901-917 (1987)); Kabat scheme (Kabat et al., Sequences of Proteins of Immunological Interest, 4th edition, U.S. Department of Health and Human Services, National Institutes of Health (1987)), AbM (University of Bath) and Contact (University College London); North scheme (North et al., A New Clustering of Antibody CDR Loop Conformations", Journal of Molecular Biology, 406, 228-256 (2011)). The boundary of the CDR of the anti-CD47 antibody in the present invention can be determined according to any schemes or a combination thereof in the art and personal evaluation.

The light chain of the antibody can be classified into one of two types (referred to as kappa (κ) and lambda (λ)) based on the amino acid sequence of the constant domain thereof. The heavy chain of the antibody can be mainly divided into 5 different types according to the amino acid sequence depending on the heavy chain constant region thereof: IgA, IgD, IgE, IgG and IgM, and several of these types can be further divided into subclasses, such as IgG1, IgG2, IgG3, IgG4, IgA1 and IgA2.

An "antibody in the form of IgG" refers to the IgG form of the heavy chain constant region of the antibody. For example, an antibody in the form of IgG4 means that the heavy chain constant region thereof is derived from IgG4.

The term "monoclonal antibody" as used herein refers to an antibody obtained from a population of substantially homogeneous antibodies, i.e., the various antibodies constituting the population are identical except for possible naturally occurring mutations that may be present in minor amounts. Monoclonal antibodies are highly specific, being directed against a single epitope. In contrast, conventional (polyclonal) antibody preparations generally include a large number of antibodies being directed against different epitopes (or specific for different epitopes). The modifier "monoclonal" indicates the feature of the antibody as being obtained from a substantially homogeneous population of antibodies, and is not to be constructed as requiring any particular method to produce the antibody.

The term "antigen-binding fragment" of an antibody as used herein includes fragments or derivatives of the antibody. Generally, the antigen-binding fragment includes at least one fragment (such as one or more CDRs) of the antigen-binding region or variable region of the antibody, and maintains at least some of the binding properties of the antibody. Examples of an antigen-binding fragment include, but are not limited to Fab, Fab', $F(ab')_2$ and Fv fragments; diabodies; linear antibodies; single-chain antibody molecules (e.g., sc-Fv); and nanobodies and multispecific antibodies formed from antibody fragments. When the antigen-binding activity is expressed on a molar concentration basis, the binding fragments or derivatives generally maintain at least 10% of the antigen-binding activity of the antibody from which they are derived. Preferably, the binding fragments or derivatives maintain at least 20%, 50%, 70%, 80%, 90%, 95% or 100% or more of the antigen binding activity of the antibody from which they are derived.

It is expected that the antibody or antigen-binding fragment thereof may include conservative or non-conservative amino acid substitutions that do not significantly change its biological activity (referred to as "conserved variants" or "functionally conserved variants" of the antibody). In a preferred aspect, conservative substitutions are derived from the conservative substitution residues shown in Table A below, preferably, the preferred conservative amino acid substitution residues shown in Table A.

TABLE A

| Original Residue | Exemplary Substitution | Preferred conservative amino acid substitution |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

An epitope is a region of an antigen that is bound by an antibody. An epitope can be formed from contiguous amino acids or non-continuous amino acids juxtaposed by tertiary folding of a protein.

The term "an isolated anti-CD47 antibody or antigen-binding fragment thereof" as used herein refers to the purified state of the anti-CD47 antibody or antigen-binding fragment thereof. For example, "isolated" may mean that the molecule is substantially free of other biomolecules, such as nucleic acids, proteins, lipids, sugars or other substances, such as cell debris and growth medium. However, as is known to a person skilled in the art, the term "isolated" does not mean the complete absence of such substances or the absence of water, buffer or salt unless they are present in an amount that significantly interferes with the experimental or therapeutic application of the antibodies described herein. In some embodiments, the isolated antibody or antigen-binding fragment can has a purity of greater than 95%, greater than 96%, greater than 97%, greater than 98% or greater than 99%, which purity is determined by, for example, electrophoresis (e.g., SDS-PAGE, isoelectric focusing (IEF), capillary electrophoresis) or chromatography (e.g., ion exchange or reverse phase HPLC). For a review of methods for evaluating antibody purity, see, for example, Flatman, S. et al., J. Chrom. B 848 (2007) 79-87.

The term "chimeric antibody" as used herein refers to an antibody having a variable domain of a first antibody and a constant domain of a second antibody, wherein the first antibody and the second antibody are from different species. Generally, the variable domain is obtained from the antibody of the experimental animals such as rodents, while the constant domain sequence is obtained from an human antibody, so that the obtained chimeric antibody is less likely to induce adverse immune response in human subjects than the antibody from the experimental animals.

The term "humanized antibody" as used herein refers to an antibody form containing sequences from human and non-human (e.g., mouse, rat) antibodies. In general, the humanized antibody comprises at least one, and generally two, variable domains, in which all or substantially all of the hypervariable loops are correspond to those of non-human immunoglobulins, and all or substantially all of the framework (FR) regions are correspond to those of human immunoglobulin. The humanized antibody can optionally comprise at least a portion of a constant region (Fc) derived from a human immunoglobulin. In some cases, as is known to a person skilled in the art, amino acid mutations can be introduced into humanized antibodies (e.g., variable domains, framework regions, and/or constant regions (if present)), for example, to improve certain properties of the antibodies; such antibody forms still fall within the scope of the "humanized antibody" of the present invention.

As is known to a person skilled in the art, the antibody may have a sugar chain of the cell for producing the antibody. For example, when produced in mice, in mouse cells, or in hybridomas derived from mouse cells, the antibody may contain a mouse sugar chain. Alternatively, when produced in rats, in rat cells, or in hybridomas derived from rat cells, the antibody may contain a rat sugar chain.

The term "Fc region" as used herein is used to define the C-terminal region of an immunoglobulin heavy chain that comprises at least a portion of the constant region. The term includes native sequence Fc region and variant Fc regions. The native sequence Fc region covers a variety of naturally occurring immunoglobulin Fc sequences, such as various Ig subtypes and allogeneic Fc regions thereof (Gestur Vidarsson et al., IgG subclasses and allotypes: from structure to effector functions, 20 Oct. 2014, doi: 10.3389/fimmu.2014.00520.). In one embodiment, the Fc region of the human IgG heavy chain extends from Cys226 or from Pro230 to the carboxyl terminus of the heavy chain. However, the lysine at the C-terminus (Lys447) of Fc region may or may not be present. Unless otherwise specified herein, amino acid residues in Fc region or constant region is numbered in accordance with the EU numbering system, also referred to EU index, as described in Kabat et al., Sequences of Proteins of Immunological Interest, 5th edition Public Health Service, National Institutes of Health, Bethesda, MD, 1991.

The terms "Fc region variant" or "variant Fc region" as used herein are used interchangeably herein, and mean that a modified Fc region is comprised relative to an Fc region of native sequence. The Fc region variants of the present invention are defined according to the amino acids modifications to the amino acids that compose them.

The term "pharmaceutical excipient" refers to a diluent, an adjuvant (e.g., Freund's adjuvant (complete and incomplete)), an excipient, a carrier or a stabilizer, etc., which is administered with an active substance.

The term "pharmaceutical composition" refers to such a composition that exists in a form that allows the biological activity of the active ingredient contained therein to be effective and does not contain additional ingredients that have unacceptable toxicity to the subject to whom the composition is administrated.

As used herein, an "immunoconjugate" is an antibody conjugated to one or more other substances, including but not limited to cytotoxic agents or labels. An "immune fusion" is an antibody which is fused by covalently linking to one or more other peptides or polypeptides.

The term "therapeutic agent" as described herein covers any substances that are effective in the prevention or treatment of related diseases, such as cancers.

The term "cytotoxic agent" as used in the present invention refers to a substance that inhibits or prevents cell function and/or causes cell death or destruction.

"Chemotherapeutic agents" include chemical small molecule drugs that are useful in the treatment of cancers or immune system diseases.

The term "small molecule drug" refers to an organic compound with a low molecular weight that can regulate biological processes. A "small molecule" is defined as a molecule with a molecular weight smaller than 10 kD, generally smaller than 2 kD and preferably smaller than 1 kD. The small molecules include but are not limited to inorganic molecules, organic molecules, organic molecules containing an inorganic component, molecules containing a radioactive atom, synthetic molecules, peptide mimics and antibody mimics. As a therapeutic agent, small molecules are better at penetrating cells than large molecules, are less susceptible to degradation, and are less likely to trigger an immune response.

The term "immunomodulator" as used herein refers to a natural or synthetic active agent or drug that regulates (suppresses or enhances) an immune response. An immune response can be a humoral response or a cellular response. An immunomodulator includes an immunosuppressant. In some embodiments, an immunomodulator comprises an active agent or a drug that enhances an immune response, for example, an active agent or a drug that is beneficial to enhancing an anticancer immune response in cancer treatment.

The "immunosuppressant", "immunosuppressive drug" or "immuno-suppressor" as used herein is a therapeutic agent for inhibiting or preventing immune system activities in immunosuppressive therapy.

The terms "carcinoma" and "cancer" refer to or describe physiological disorders in mammals, generally characterized by unregulated cell growth. This definition includes benign and malignant cancers and resting tumors or micrometastasis. The "cancer" includes, but is not limited to, solid tumors and hematological cancer. Examples of various cancers include, but are not limited to, carcinoma, lymphoma, blastoma, sarcoma and leukemia.

The term "vector" as used herein refers to any recombinant polynucleotide constructs that can be used for the purpose of transformation (i.e. introduction of heterologous DNA into host cells). One type of the vector is a "plasmid", which is a circular double stranded DNA loop, by which additional DNA segments can be ligated into the loop. Another type of the vector is a viral vector, by which additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. In addition, some vectors can guide the expression of genes that are operably linked. Such vectors are referred to as "expression vector" herein. The expression vector refer to the nucleic acid that can replicate and express a target gene when the vector is transformed, transfected or transduced into a host cell. The expression vector comprises one or more phenotypic selectable markers and origins of replication to ensure vector maintenance and provide amplification in the host if necessary.

The term "subject" or "patient" or "individual" herein includes any human or non-human animals. The term "non-human animal" includes all vertebrates, such as mammals and non-mammals, such as non-human primates, sheep, dogs, cats, horses, bovine, chicken, amphibians, reptiles, etc.

The terms "therapeutically effective amount", "therapeutically effective dose" and "effective amount" herein refer to the amount of the anti-CD47 antibody or antigen-binding fragment thereof of the present invention that effectively prevents or improves the symptoms of one or more diseases or conditions or the development of the diseases or conditions when given to cells, tissues or subjects alone or in combination with other therapeutic drugs. Therapeutically effective dose also refers to the amount of the antibody or antigen-binding fragment thereof that is sufficient to result in improvement of the symptoms, such as the amount to treat, cure, prevent or improve related medical conditions or to increase the speed of treatment, cure, prevention or improvement of such conditions. When the active ingredient alone is administered to an individual, the therapeutically effective dose refers only to the ingredient. When administered in combination, the therapeutically effective dose refers to the comprehensive amount of active ingredients contributing to therapeutic effects, regardless of administration in combination, in sequence or at the same time. The effective amount of the therapeutic agent will result in an increase in the diagnostic criteria or parameter by at least 10%, generally at least 20%, preferably at least about 30%, more preferably at least 40%, and most preferably at least 50%.

As used herein, "treatment" includes 1) therapeutic measures, which cure, alleviate and relieve the symptoms of the diagnosed pathological condition or disease and/or stop the progress of the diagnosed pathological condition or disease. Therefore, the subject receiving the treatment includes an individual who has suffered from the disease. In some embodiments, the present invention relates to the treatment of a disease or condition.

In some embodiments according to the present invention, the "treatment" of a disease or condition refers to the improvement of the disease or condition (i.e., alleviating or preventing or reducing the progression of the disease or at least one of its clinical symptoms). In some other embodiments, "treatment" refers to relieving or improving at least one body parameter, including those physical parameters that may not be discernible by the patient. In some other embodiments, "treatment" refers to the regulation of a disease or condition physically (e.g., stabilization of discernible symptoms), physiologically (e.g., stabilization of body parameters), or both. Methods for evaluating the treatment of a disease are generally known in the art unless explicitly described herein.

In yet other embodiments according to the present invention, "prevention" of a disease or condition includes inhibition of the occurrence or development of the disease or condition or the symptom of a particular disease or condition. In some embodiments, a subject with a family history of cancer is a candidate for a prophylactic regimen. Generally, in the context of cancer, the term "prevention" refers to administration of drugs to a subject prior to the onset of conditions or symptoms of cancer, in particular, in a subject at risk of cancer.

In some embodiments, after "treating" the cancer by the method of the present invention, an individual patient is considered to have been successfully treated if the individual shows one or more of the following: the number of cancer cells was decreased or cancer cells disappeared completely; tumor size was decreased; infiltration of cancer cells into peripheral organs was inhibited or absent, including, for example, the spread of cancer cells to soft tissues and bones; tumor metastasis was inhibited or absent; tumor growth was inhibited or absent; one or more symptoms associated with the specific cancer were relieved; incidence and mortality were reduced; the quality of life was improved; the tumor incidence, frequency or tumorigenicity was reduced; the number or frequency of cancer stem cells in tumor was reduced; tumor cells were differentiated into a non-tumorigenic state; or a combination of some of the effects.

"Inhibition of tumor growth" refers to any mechanism by which tumor cell growth can be inhibited. In some embodiments, tumor cell growth is inhibited by delaying tumor cell proliferation. In some embodiments, tumor cell growth is inhibited by stopping tumor cell proliferation. In some embodiments, tumor cell growth is inhibited by killing tumor cells. In some embodiments, tumor cell growth is inhibited by inducing tumor cell apoptosis. In some embodiments, tumor cell growth is inhibited by inducing tumor cell differentiation. In some embodiments, tumor cell growth is inhibited by depriving tumor cells of nutrients. In some embodiments, tumor cell growth is inhibited by preventing tumor cell migration. In some embodiments, tumor cell growth is inhibited by preventing tumor cell invasion.

As used herein, "sequence identity" refers to the degree of identity of sequences based on one by one nucleotide or amino acid comparing in the comparison window. The "(percentage) sequence identity" can be calculated as follows: comparing the two optimally aligned sequences in the comparison window, determining the number of positions with the same nucleic acid base (e.g., A, T, C, G, I) or the same amino acid residue (e.g., Ala, Pro, Ser, Thr, Gly, Val, Leu, Ile, Phe, Tyr, Trp, Lys, Arg, His, Asp, Glu, Asn, Gln, Cys and Met) in the two sequences to obtain the number of matching positions, dividing the number of matching positions by the total number of positions in the comparison window (i.e., window size), and multiplying the result by 100 to yield the percentage of sequence identity. Optimal alignment for purposes of determining the percentage of sequence identity can be achieved in various ways known in the art, for example, using publicly available computer softwares such as BLAST, BLAST-2, ALIGN or MEGALIGN (DNASTAR) software. Those skilled in the art is able to determine appropriate parameters for aligning sequences, including any algorithms needed to achieve maximal alignment over the full-length of the sequences or the target sequence area being compared. In the present invention, for antibody sequences, the percentage of identity of amino acid sequences is determined by optimally aligning the candidate antibody sequence with the reference antibody sequence, and then performing an optimal alignment in accordance with a kabat numbering rule in a preferred embodiment.

The term "agglutination" as used herein refers to cell agglomeration, and the term "hemagglutination" refers to agglomeration of a particular class of cells (i.e., red blood cells). Therefore, hemagglutination is a type of agglutination.

The control antibody "Hu5F9" herein is an anti-CD47 antibody in the form of IgG4P, formed by recombinant expression by GenScript according to the variable region sequence of 5F9 disclosed in patent US 2015/0183874 A1. The control antibody "SRF231" is an anti-CD47 antibody in the form of IgG4P, formed by recombinant expression by GenScript according to the variable region sequence of 2.3D11 disclosed in patent US 20180201677 A1.

Anti-CD47 Antibody and Production Thereof

The antibody of the present invention can be produced by any suitable method for producing an antibody. Any suitable form of CD47 can be used as an immunogen (antigen) to produce antibodies. By way of example and not limitation, any CD47 variant or fragment thereof can be used as an immunogen. In some embodiments, hybridoma cells producing murine monoclonal anti-human CD47 antibodies may be produced by methods well-known in the art. These methods include but are not limited to the hybridoma technique originally developed by Kohler et al., (1975) (Nature 256: 495-497). Preferably, according to a standard protocol, mouse spleen cells were isolated and fused with mouse myeloma cell line by PEG or electrofusion. Then, hybridoma cells secreting an antibody with a CD47 binding activity were screened. The DNA sequence of the immunoglobulin variable region of hybridoma cells of the present invention can be detected by the method based on a degenerate primer PCR.

Antibodies from rodents (such as mice) may cause undesired antibody immunogenicity when used as therapeutic drugs in vivo. Repeated use causes an immune response against therapeutic antibodies in humans. This kind of immune response will at least lead to the loss of therapeutic efficacy, and in severe cases, lead to potentially lethal allergic reaction. One method of reducing the immunogenicity of rodent antibodies includes the production of chimeric antibodies, in which a mouse antibody variable region is fused with a human constant region (Liu et al. (1987) Proc. Natl. Acad. Sci. USA 84: 3439-43). However, the retention of intact rodent variable regions in chimeric antibodies can still cause harmful immunogenicity in patients.

Transplantation of CDR from a rodent variable region into a human framework (i.e., humanization) has been used to further minimize a rodent sequence. For the humanized antibody of the present invention, murine CDR regions can be inserted into a human germline framework using a method known in the art. See Winter et al., U.S. Pat. No. 5,225,539 and Queen et al., U.S. Pat. Nos. 5,530,101; 5,585,089; 5,693,762 and 6,180,370. However, the CDR loop exchange can not produce an antibody with the same binding property as an original antibody. In a humanized antibody, it often needs to further change framework residues (FR) (residues involved in the support of CDR loop) to maintain an antigen binding affinity. Kabat et al. (1991) J. Immunol. 147: 1709. In short, the humanized transformation process involves the following steps: A. the gene sequence of each candidate antibody is aligned with the gene sequence of a human embryonic antibody to find the sequence with high homology; B. the HLA-DR affinity is analyzed and investigated to select a human embryonic framework sequence with low affinity; C. the framework amino acid sequences of the variable region and its surrounding region are analyzed by using computer simulation technology and molecular docking, and their spatial stereoscopic binding mode is investigated. By calculating electrostatic force, van der Waals force, hydrophilicity and entropy, the key amino acid individuals that may interact with CD47 and maintain the spatial framework in the candidate antibody gene sequence are analyzed and grafted back to the selected human embryonic gene framework, the amino acid positions in the framework region that must be reserved are marked on this basis, and the humanized antibody is synthesized.

The accurate amino acid sequence boundary of the variable region CDR of the antibody of the present invention can be determined by using any one of many well known schemes such as Kabat, Chothia, AbM, Contact or North. It should be noted that the boundary of CDR of the variable region of the same antibody obtained by different definition systems may be different. That is, the CDR sequences of the variable region of the same antibody defined by different assignment systems are different. Therefore, when it comes to defining an antibody with a specific CDR sequence as defined in the present invention, the scope of the antibody also covers an antibody, the variable region sequence of which comprises the specific CDR sequence. However, due to the application of different schemes (such as different assignment systems or combinations), the claimed CDR boundary is different from the specific CDR boundary as defined in the present invention.

In some embodiments, the CDR boundary of the anti-CD47 antibody molecule provided by the present invention is determined based on the Kabat assignment system.

Antibodies with different specificities (i.e., different binding sites for different antigens) have different CDRs. However, although CDR is different from antibody to antibody, only a limited number of amino acid positions in CDR are directly involved in antigen binding. The minimum overlapping region can be determined using at least two of the Kabat, Chothia, AbM and North methods to provide a "minimum binding unit" for antigen binding. The minimum binding unit can be a subset of CDR. As is appreciated by a person skilled in the art, the residues of the rest of the CDR sequence can be determined according to the structure and protein folding of the antibody. Therefore, the present invention also contemplates any variants of the CDR presented herein. In some embodiments, in a variant of CDR of the anti-CD47 antibody or antigen-binding fragment thereof of the present invention, the amino acid residue of the minimum binding unit can remain unchanged, while the residues of the rest of the CDR defined according to Kabat or IMGT can be replaced by conservative amino acid residues.

In some embodiments, the anti-CD47 antibody or antigen-binding fragment thereof provided by the present invention comprises one to three selected from heavy chain complementary determining region 1(HCDR1), HCDR2 and HCDR3, wherein the HCDR1 comprises an amino acid sequence that is identical to the amino acid sequence of SEQ ID NO: 11 or has at least 1 and no more than 3, 2 or 1 amino acid changes (preferably amino acid substitutions, preferably conservative substitutions) compared with the amino acid sequence of SEQ ID NO: 11, the HCDR2 comprises an amino acid sequence that is identical to the amino acid sequence of SEQ ID NO: 12 or has at least 1 and no more than 3, 2 or 1 amino acid changes (preferably amino acid substitutions, preferably conservative substitutions) compared with the amino acid sequence of SEQ ID NO: 12, and the HCDR3 comprises an amino acid sequence that is identical to the amino acid sequence of SEQ ID NO: 13 or SEQ ID NO: 17 or SEQ ID NO: 21 or has at least 1 and no more than 3, 2 or 1 amino acid changes (preferably amino acid substitutions, preferably conservative substitutions) compared with the amino acid sequence of SEQ ID NO: 13 or SEQ ID NO: 17 or SEQ ID NO: 21.

In some embodiments, the anti-CD47 antibody or antigen-binding fragment thereof provided by the present invention comprises one to three selected from light chain complementary determining region 1 (HCDR1), LCDR2 and LCDR3, wherein the LCDR1 comprises an amino acid sequence that is identical to the amino acid sequence of SEQ ID NO: 14 or has at least 1 and no more than 3, 2 or 1 amino acid changes (preferably amino acid substitutions, preferably conservative substitutions) compared with the amino acid sequence of SEQ ID NO: 14, the LCDR2 comprises an amino acid sequence that is identical to the amino acid sequence of SEQ ID NO: 15 or SEQ ID NO: 18 or SEQ ID NO: 22 or has at least 1 and no more than 3, 2 or 1 amino acid changes (preferably amino acid substitutions, preferably conservative substitutions) compared with the amino acid sequence of SEQ ID NO: 15 or SEQ ID NO: 18 or SEQ ID NO: 22, and the LCDR3 comprises an amino acid sequence that is identical to the amino acid sequence of SEQ ID NO: 16 or has at least 1 and no more than 3, 2 or 1 amino acid changes (preferably amino acid substitutions, preferably conservative substitutions) compared with the amino acid sequence of SEQ ID NO: 16.

In some embodiments, the anti-CD47 antibody or antigen-binding fragment thereof provided by the present invention also covers an antibody or an antigen-binding fragment thereof, in the three CDRs of the heavy chain variable region of which, relative to the three CDRs specifically disclosed herein, a total of at least one and no more than 5, 4, 3, 2 or 1 amino acid changes (preferably amino acid substitutions, preferably conservative substitutions) is comprised, and/or in the three CDRs of the light chain variable region of which, relative to the three CDRs specifically disclosed herein, a total of at least one and no more than 5, 4, 3, 2 or 1 amino acid changes (preferably amino acid substitutions, preferably conservative substitutions) is comprised.

In some embodiments, the anti-CD47 antibody or antigen-binding fragment thereof provided by the present invention also covers such an antibody or antigen-binding fragment thereof, wherein compared with the heavy chain variable region and/or light chain variable region of the antibody specifically disclosed herein, there are one or more (preferably no more than 10, more preferably no more than 6, 5, 4, 3, 2 or 1) amino acid changes (preferably amino acid substitutions, more preferably amino acid conservative substitutions) in the heavy chain variable region and/or light chain variable region, and preferably, the amino acid change does not occur in the CDR region.

In some embodiments, the anti-CD47 antibody or antigen-binding fragment thereof provided by the present invention comprises a heavy chain variable region (VH) comprising an amino acid sequence identical to or having at least 90%, 91%, 92%, 93%, 94%, 95%, 96%, 97%, 98% or 99% sequence identity to the amino acid sequence selected from SEQ ID NO: 1, 3, 5, 6 or 7. In some embodiments, the anti-CD47 antibody or antigen-binding fragment thereof of the present invention comprises a light chain variable region (VL) comprising an amino acid sequence identical to or having at least 90%, 91%, 92%, 93%, 94%, 95%, 96%, 97%, 98% or 99% sequence identity to the amino acid sequence selected from SEQ ID NO: 2, 4, 8, 9 or 10.

In an embodiment of the present invention, the amino acid changes described herein include amino acid substitutions, insertions or deletions. Preferably, the amino acid changes described herein are amino acid substitutions, preferably conservative substitutions.

In a preferred embodiment, the amino acid changes of the present invention occur in regions outside CDRs (for example, in FRs). More preferably, the amino acid changes of the present invention occur in regions outside the heavy chain variable region and/or outside the light chain variable region. In some embodiments, the amino acid changes occur in a heavy chain constant region and/or a light chain constant region.

In some embodiments, the antibodies of the present invention comprising amino acid changes have comparable or similar properties to the specific antibodies disclosed herein.

In some embodiments, the anti-CD47 antibody of the present invention includes post-translational modifications to CDRs, light chain variable regions, heavy chain variable regions, light chains, or heavy chains.

In some embodiments, the anti-CD47 antibody provided by the present invention is a full-length antibody, a single-domain antibody such as a VHH, a Fab antibody, a Fab' antibody, a Fab'-SH, a $(Fab')_2$ antibody, a single-chain antibody such as a scFv, a Fv, a dAb (domain antibody) or a bis (multi)-specific antibody.

In some embodiments, the anti-CD47 antibody provided by the present invention is any antibody in the form of IgG, such as an antibody in the form of IgG1, IgG2, IgG3 or IgG4. In some embodiments, the anti-CD47 antibody of the present invention is an antibody in the form of IgG4P, i.e., a modification, Ser228Pro (S228P, numbered according to EU) is carried out in the hinge region of the human IgG4 constant region to avoid or reduce chain exchange.

In some embodiments, one or more amino acid modifications can be introduced into the Fc region of the antibody provided by the present invention to produce Fc region variants. The Fc region variant can comprise a human Fc region sequence (such as the Fc region of human IgG1, IgG2, IgG3, or IgG4) containing amino acid modifications (such as substitutions) at one or more amino acid positions, for example, a number of modifications to human IgG1 to enhance or reduce its binding to FcγR and enhance or reduce the corresponding function are summarized in article of Bruhns and Jönsson published in Immunol Rev. 2015 November; 268 (1): 25-51, page 44.

In some embodiments, the anti-CD47 antibody provided by the present invention comprises an Fc region variant, which has a Fc γ R binding activity which is reduced or deficient. In some embodiments, the Fc region variant has amino acid substitutions, and in particular, the amino acid substitutions are selected from other amino acid substitutions at positions E233, L234, L235, N297, and P331 of an immunoglobulin heavy chain. In some embodiments, the amino acid substitutions of the Fc region variant are E233P, L234A, L235A, L235E, N297A, N297D or P331S.

In some embodiments, the antibody provided herein is modified to increase or decrease the degree of glycosylation of the antibody. The addition or deletion of glycosylation sites of an antibody can be conveniently achieved by changing the amino acid sequence so as to produce or remove one or more glycosylation sites. Glycosylation can be changed, for example, to increase affinity of the antibody for the "antigen". This modification can be accomplished, for example, by changing one or more glycosylation sites within the antibody sequence. For example, one or more amino acid substitutions can be made, which results in the elimination of one or more variable region framework glycosylation sites, thereby eliminating glycosylation at this site. This aglycosylation can increase affinity of the antibody for the antigen. Such a method is described in, for example, U.S. Pat. No. 5,426,300. When the antibody comprises an Fc region, the saccharides attached to same can be changed. In some applications, modifications to remove undesired glycosylation sites are useful, such as removal of fucose modules to improve antibody-dependent cell-mediated cytotoxicity (ADCC) functions. In other applications, galactosylation modification can be made to modify complement-dependent cytotoxicity (CDC).

In some embodiments, it may be desirable to create cysteine engineered antibodies, e.g., "thioMAbs," in which one or more residues of an antibody are substituted with cysteine residues.

In some embodiments, the antibody provided herein may be further modified to comprise additional non-protein moieties that are known in the art and readily available. The non-protein moieties include, but are not limited to, water soluble polymers. Non-limiting examples of water soluble polymers include, but are not limited to, polyethylene glycol (PEG), ethylene glycol/propylene glycol co-polymers, carboxymethylcellulose, dextran, polyvinyl alcohol, polyvinyl pyrrolidone, poly-1,3-dialkane, poly-1,3,6-trialkane, ethylene/maleic anhydride co-polymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols (e.g., glycerol), polyvinyl alcohol, and mixtures thereof.

Antibody Expression

The present invention relates to a host cell comprising one or more expression vectors and a method for producing any antibody or antigen-binding fragment thereof of the present invention, wherein the method comprises culturing the host cell, purifying and recovering the antibody or antigen-binding fragment.

In one aspect, the present invention provides a nucleic acid encoding any of the above anti-CD47 antibodies or antigen-binding fragments thereof. For example, the present invention provides a nucleic acid encoding heavy chains, light chains, variable regions or complementarity determining regions described herein. In some aspects, the nucleic acid encoding the heavy chain variable region has at least 85%, 89%, 90%, 91%, 92%, 93%, 94%, 95%, 96%, 97%, 98%, 99% or 100% sequence identity to the nucleic acid as set forth in SEQ ID NO: 19. In some aspects, the nucleic acid encoding the light chain variable region has at least 85%, 89%, 90%, 91%, 92%, 93%, 94%, 95%, 96%, 97%, 98%, 99% or 100% sequence identity to the nucleic acid as set forth in SEQ ID NO: 20.

In one aspect, one or more vectors comprising the nucleic acid are provided. In some embodiments, the vector is an expression vector. The selection of an expression vector depends on the intended host cell in which the vector is to be expressed. Generally, an expression vector comprises a promoter and other regulatory sequences (e.g., enhancers) operably linked to a nucleic acid encoding an anti-CD47 antibody chain or antigen-binding fragment thereof. In some embodiments, the expression vector further comprises a sequence encoding the antibody constant region. In some embodiments, the expression vector is a PTT5 vector or a pCDNA vector, such as pCDNA3.4.

In one aspect, the present invention provides host cells for expressing the recombinant antibodies of the present invention, including prokaryotic or eukaryotic cells. In some embodiments, *Escherichia coli* is a prokaryotic host that can be used to clone and express the polynucleotides of the present invention. Other suitable microbial hosts include bacilli, such as *Bacillus subtilis*, and other Enterobacteriaceae, such as *Salmonella, Serratia*, and various *Pseudomonas*. In these prokaryotic hosts, expression vectors can also be prepared, which generally comprise expression control sequences (for example, an origin of replication) that are compatible with the host cells. In some embodiments, mammalian host cells are used to express and produce the anti-CD47 antibody polypeptides of the present invention. For example, they may be hybridoma cell lines expressing endogenous immunoglobulin genes, or mammalian cell lines with exogenous expression vectors, including normal human cells, or immortalized animal or human cells. For example, many suitable host cell lines capable of secreting intact immunoglobulin have been developed, including CHO cell lines, various COS cell lines, Expire293 cells, HEK293 cells, myeloma cell lines, transformed B cells and hybridomas.

In one aspect, the present invention provides a method for preparing an anti-CD47 antibody, wherein the method comprises introducing an expression vector into a mammalian host cell, and allowing the antibody to be expressed in the host cell by culturing the host cell for a sufficient period of time, or more preferably, secreting the antibody into the medium in which the host cell is grown to produce the antibody. Standard protein purification methods can be used to recover antibodies from the culture medium. The antibody molecule prepared as described herein can be purified by known available techniques such as high performance liquid chromatography, ion exchange chromatography, gel electrophoresis, affinity chromatography, size exclusion chromatography, etc. The actual conditions used to purify a specific protein also depend on factors such as net charge, hydrophobicity, and hydrophilicity, which are obvious to a person skilled in the art. The purity of the antibody molecule of the present invention can be determined by any of a variety of well-known analytical methods, including size exclusion chromatography, gel electrophoresis, high performance liquid chromatography, etc.

Antibodies expressed by different cell lines or expressed in transgenic animals are likely to have different glycosylation from each other. However, all antibodies encoding by the nucleic acids provided herein or comprising the amino acid sequences provided herein are constituents of the present invention, regardless of the glycosylation of the antibodies.

Determination Method

The physical/chemical properties and/or biological activities of the anti-CD47 antibody provided herein can be identified, screened, or characterized by a variety of determination methods known in the art. In one aspect, the antigen-binding activity of the antibody of the present invention is tested, for example, by a known method such as ELISA and Western blot. Methods known in the art can be used to determine binding to CD47, and exemplary methods are disclosed herein.

The present invention also provides an determination method for identifying anti-CD47 antibodies with biological activities. The biological activities can include, for example, binding to CD47 (for example, binding to human CD47), binding to CD47 on a cell surface, blocking the binding of CD47 to a ligand thereof, effects on the activity in promoting red blood cell agglutination, and effects on phagocytosis of tumor cells by human macrophages, etc. Also provided are antibodies having such biological activities in vivo and/or in vitro. In certain embodiments, the antibodies of the present invention are tested for such biological activities.

Cells for use in any of the above-mentioned in vitro determination methods include cell lines that naturally express CD47 or are engineered to express CD47, such as tumor cell lines. Such cells also include cell lines that express CD47 and cell lines transfected with DNA encoding the CD47 that express CD47 under abnormal circumstances.

It can be understood that the immunoconjugates or immune fusions of the present invention can be used to replace or supplement the anti-CD47 antibody to perform any of the above-mentioned determination methods.

It can be understood that a combination of an anti-CD47 antibody and other active agents can be used to perform any of the above-mentioned determination methods.

Immunoconjugate and Immune Fusion

In some embodiments, the present invention provides an immunoconjugate, comprising any anti-CD47 antibody or antigen-binding fragment thereof provided by the present invention and other substances. In one embodiment, the other substances are, for example, a cytotoxic agent, which includes any agent that is harmful to cells.

In some embodiments, the present invention provides immune fusion comprising any anti-CD47 antibody or antigen-binding fragment thereof provided herein.

In some embodiments, the immunoconjugate and the immune fusion are used for preventing or treating CD47-related diseases.

Pharmaceutical Composition

The term "pharmaceutical composition" refers to such a preparation/formulation that allows the active ingredient contained therein existing in a form to be biological activity effective and does not contain additional ingredients that have unacceptable toxicity to the subject to whom the preparation/formulation is administrated.

The term "pharmaceutical excipient" refers to a pharmaceutical carrier, a diluent, an adjuvant (e.g., Freund's adjuvant (complete and incomplete)), or an excipient, which is administered with a therapeutic agent.

The pharmaceutical composition of the present invention may include the antibody of the present invention and a pharmaceutical excipient. These pharmaceutical compositions can be included in kits, such as diagnostic kits.

As used herein, a "pharmaceutical carrier" includes any and all solvents, dispersion medium, isotonic agents, absorption delaying agents, etc., that are physiologically compatible. Pharmaceutical carriers suitable for the present invention can be sterile liquids, such as water and oils, including those of petroleum, animal, vegetable or synthetic origin, such as peanut oil, soybean oil, mineral oil, sesame oil, etc. Water is a preferred carrier when the pharmaceutical composition is administered intravenously. It is also possible to use saline solutions, aqueous dextrose and glycerol solutions as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dry skim milk, glycerol, propylene, diol, water, ethanol, etc. For the application of excipients and uses thereof, see also "Handbook of Pharmaceutical Excipients", fifth edition, R. C. Rowe, P. J. Seskey and S. C. Owen, Pharmaceutical Press, London, Chicago. The composition may also contain a small amount of a wetting agent or an emulsifier, or a pH buffering agent. These compositions can be in the form of solutions, suspensions, emulsions, tablets, pills, capsules, powders, sustained release agents, etc. Oral formulation can comprise standard carriers such as pharmaceutical grades of mannitol, lactose, starch, magnesium stearate, saccharin, etc.

The present invention provides a pharmaceutical composition comprising one or more monoclonal antibodies binding to CD47 or antigen-binding fragments thereof, and nucleic acids, vectors or host cells, or immunoconjugates or fusions of the present invention. It should be understood that the anti-CD47 antibodies, or an antigen-binding fragment, a nucleic acid, a vector or a host cell thereof, or an immunoconjugate, or a fusion, or a pharmaceutical composition thereof provided by the present invention can be integrated with suitable pharmaceutical carriers, excipients and other reagents in the preparation for co-administration, so as to provide improved transfer, delivery, tolerance, etc.

The pharmaceutical preparation/formulation comprising the anti-CD47 antibody described herein can be prepared by mixing the anti-CD47 antibody or antigen-binding fragment thereof of the present invention having the desired degree of purity with one or more optional pharmaceutical excipients, preferably in the form of aqueous solutions or lyophilized preparations. Exemplary lyophilized antibody preparations/formulations are described in U.S. Pat. No. 6,267,958. Aqueous antibody preparations/formulations include those described in U.S. Pat. No. 6,171,586 and WO 2006/044908, the latter preparation/formulation including a histidine-acetate buffering agent.

The pharmaceutical compositions or preparations/formulations of the present invention may also comprise one or more other active ingredients that are required for the treatment of specific diseases, preferably those active ingredients with complementary activities that do not adversely affect each other. For example, it is desirable that other therapeutic agents are also included. In some embodiments, the other therapeutic agents are chemotherapeutic agents, radio therapeutic agents, cytokines, vaccines, other antibodies, immunomodulators or other biomacromolecular drugs.

In some embodiments, the pharmaceutical composition of the present invention may also comprise nucleic acids encoding the anti-CD47 antibody or an antigen-binding fragment thereof.

Methods and Uses

In one aspect, the present invention provides a method for preventing, diagnosing or treating CD47-related diseases in a subject. The method comprises administering to a patient in need thereof an effective amount of the anti-CD47 antibody or antigen-binding fragment thereof described herein, or an immunoconjugate or a immune fusion or a pharmaceutical composition comprising same, or a nucleic acid, a vector or a host cell described herein.

In one aspect, the present invention provides the use of the anti-CD47 antibodies or antigen-binding fragments thereof in the production or preparation of drugs for the prevention, diagnosis or treatment of CD47-related diseases in subjects.

In one aspect, the anti-CD47 antibodies, and antigen-binding fragments thereof, and pharmaceutical compositions comprising same provided by the present invention can be used as therapeutic agents to prevent or treat CD47-related diseases in subjects. For CD47-related diseases in subjects identified by using standard methods, the anti-CD47 antibodies and antigen-binding fragments thereof, and pharmaceutical compositions or immunoconjugates or immune fusion comprising same disclosed in the present invention, or the nucleic acids, vectors or host cells described herein can be administered.

In some embodiments, the methods and uses described herein further comprise administering to the individual an effective amount of at least one additional therapeutic agent or therapeutic mode. In some embodiments, the therapeutic agents are, for example, chemotherapeutic agents, radio therapeutic agents, cytokines, vaccines, other antibodies, immunomodulators or other biomacromolecular drugs. In some embodiments, the therapeutic mode includes surgery; and radiation therapy, local irradiation or focus irradiation, etc.

The above-mentioned combination therapy includes combined administration (in which two or more of therapeutic agents are contained in the same or separate preparations/formulations) and separate administration, wherein the administration of the anti-CD47 antibody or antigen-binding fragment thereof of the present invention may occur prior to, simultaneously with, or after administration of additional therapeutic agent and/or adjuvant and/or treatment.

In some embodiments, the CD47-related diseases of the present invention refer to diseases related to abnormal CD47 expression, activity and/or signal transmission in a subject, including but not limited to cancer. In some embodiments, in CD47-related diseases, the (level or content) of nucleic acid encoding CD47 is increased, or CD47 expression is increased, or CD47 protein level is increased, or activity is increased, or activity signal transmission is increased.

In some embodiments, the treatment of the disease will benefit from the inhibition of CD47 in nucleic acid or protein levels, or benefit from blocking of the binding of CD47 to its ligand or CD47-mediated signal transmission.

In some embodiments, the subject may be a mammal, e.g., a primate, preferably a higher primate, e.g., a human (e.g., an individual suffering from a disease described herein or having a risk of suffering from a disease described herein). In one embodiment, the subject suffers from or has a risk of suffering from a disease described herein (e.g., cancer). In certain embodiments, the subject receives or has received other treatments, such as chemotherapy and/or radiation therapy.

In some embodiments, the cancer includes various hematological cancer and solid tumors, and metastatic lesions. In one embodiment, examples of solid tumors include malignant tumors. The cancer can be at an early stage, a middle stage or a late stage, or a metastatic cancer. The cancer is, for example, bladder cancer, pancreatic cancer, lymphomas, leukemia, multiple myeloma, (malignant) melanoma, liomyoma, leiomyosarcomas, glioma, glioblastoma, myeloma, endometrial cancer, renal carcinoma, (benign) melanoma, prostate cancer, thyroid carcinoma, cervical cancer, gastric cancer, or liver cancer. In some embodiments, the lymphoma is selected from Burkitt lymphoma, diffuse large cell lymphoma, or mantle cell lymphoma. In some embodiments, the leukemia is promyelocytic leukemia.

The antibody or antigen-binding fragment of the present invention may be administered in any suitable manner, including oral, parenteral, intrapulmonary and intranasal administration, and, if topical treatment is needed, it can be administered intralesionally. Parenteral infusion includes intramuscular, intravenous, intraarterial, intraperitoneal or subcutaneous administration. Administration can be carried out by any suitable route, for example by injection, such as intravenous or subcutaneous injection, depending in part on whether the administration is short-lived or long-term. Various administration regimens are contemplated herein, including but not limited to single or multiple administrations at various time points, bolus administration, and pulse infusion.

The antibody or antigen-binding fragment of the present invention will be formulated and administered in a manner consistent with good medical practice. Not necessarily, but optionally, the antibody is formulated with one or more agents currently used to prevent or treat the disease. The effective amount of these other agents depends on the amount of antibody present in the preparation/formulation, the type of condition, or disease to be treated, and other factors discussed above. In order to prevent or treat diseases, the antibody or antigen-binding fragment of the present invention will be administered in a suitable dose depending on the type of diseases to be treated, the type of antibodies, the severity and course of the disease, whether the antibody is for the purpose of prevention or treatment, the previous treatment, the patient's clinical history and response to antibodies and the judgment of the attending physician. The antibody is appropriately administered to the patient at one time or over a series of treatments.

In certain embodiments, any anti-CD47 antibody or antigen-binding fragment thereof provided herein can be used to detect the presence of CD47 in a sample. In some embodiments, the detection method includes:

(a) contacting the sample with the antibody, or an antigen-binding fragment or conjugate or fusion thereof of the present invention; and (b) detecting the formation of the complex of the antibody or antigen-binding fragment thereof or the conjugate or the fusion and the CD47 protein.

The term "detection" when used herein includes quantitative or qualitative detection. In certain embodiments, the sample is blood, serum, or other liquid samples of biological origin. In certain embodiments, the sample comprises cells or tissues. In some embodiments, the sample is from hyperproliferative or cancerous focus related focus.

In one embodiment, the antibody or antigen-binding fragment thereof of the present invention can be used to diagnose CD47-related diseases, such as cancer, for example to evaluate (e.g., monitor) the treatment or progression of the diseases described herein, and diagnosis and/or staging thereof in an individual. In certain embodiments, a labeled anti-CD47 antibody or antigen-binding fragment thereof is provided. Labels include, but are not limited to, labels or parts that are directly detected (such as fluorescent labels, chromophore labels, electron-dense labels, chemiluminescent labels, and radioactive labels), and parts that are indirectly detected, such as enzymes or ligands, for example, by enzymatic reactions or intermolecular interactions. In some embodiments, provided herein is a kit for diagnosing CD47-related diseases, which kit comprises the antibody or antigen-binding fragment thereof of the present invention.

In some embodiments provided herein, the sample is obtained prior to treatment with the anti-CD47 antibody or antigen-binding fragment thereof. In some embodiments, the sample is obtained prior to treatment with other therapies. In some embodiments, the sample is obtained during or after treatment with other therapies.

The present invention includes any combinations of specific embodiments described herein. It should be understood that although the specific content and examples are described to illustrate the preferred embodiments of the present invention, these are merely illustrative and used as examples. The present invention further covers embodiments modified on the basis of the preferred embodiments of the present invention that are obvious to a person skilled in the art. For all purposes, all publications, patents and patent applications cited herein, including citations, will be incorporated herein by reference in their entirety.

DETAILED DESCRIPTION OF EMBODIMENTS

Example 1 Preparation and Screening of Hybridoma-Derived Antibody

The anti-CD47 antibodies were obtained by hybridoma technique. The recombinant protein CD47-Fc (ACROBiosystems, Cat: CD7-H5256) containing the extracellular domain of human CD47 with a Fc tag was used as an antigen to immunize mice. After mixing and emulsifying the recombinant protein CD47-Fc with complete or incomplete Freund's adjuvant (Sigma-Aldrich), SJL mice (Beijing Vital River Laboratory Animal Technology Co., Ltd) and BALB/c mice (Yangzhou University Medical Center) were immunized. The mice were subjected to one round of immunization (complete Freund's adjuvant) and two rounds of booster immunization (incomplete Freund's adjuvant) and taken blood after each booster immunization. The binding activity of the serum of the mice after immunization to the recombinant human CD47-Fc (ACROBiosystems, Cat: CD7-H5256) protein is detected by ELISA assay, and at the same time, the binding potency of mice serum to CHO cells (constructed by GenScript) overexpressing human CD47 was detected by flow cytometry (FACS). Spleen cells of the mice with a higher serum titer were selected to fuse with myeloma cell line SP2/0 (ATCC). Four days before fusion, the recombinant protein CD47-Fc of human CD47 extracellular domain was intraperitoneally injected into mice for booster immunization. On the day of fusion, mice were euthanized, and then mouse spleen cells were homogenized to obtain a single cell suspension. The mouse spleen cells were fused with murine myeloma cell line SP2/0 (3:1) by means of an electrofusion apparatus. The fused cells were resuspended in a medium containing HAT (hypoxanthine, aminopterin and thymidine deoxynucleotide, GIBCO, Cat: 21060016) to screen the successfully fused hybridoma cells. The supernatant of hybridoma cells was collected and the hybridoma cells that secreted antibodies specifically binding to human CD47 were screened by two rounds of ELISA. Then, the activity of secretion supernatant of the hybridoma was determined by CD47-related functional screening tests (such as binding specificity with human CD47 or cynomolgus monkey CD47; no activity in induction of red blood cell agglutination; activity in promoting phagocytosis of tumor cells by macrophages), and then the positive hybridoma clones were selected and subcloned for single or multiple rounds to obtain monoclone. After screening, 125G4A4 was finally chosen as a hybridoma clone.

The candidate hybridoma cell 125G4A4 was subjected to an expanded culture, and after 7-10 days of culturing, the supernatant was collected, centrifuged and filtered to remove cells and debris. The supernatants were passed through a Protein A purification column (GenScript), then cleaned and equilibrated with a buffer containing 0.05 M Tris and 1.5 M NaCl (pH 8.0), and then eluted with 0.1 M sodium citrate (pH 3.5); and the eluent was immediately neutralized with one ninth volume of 1 M Tris-HCl (pH 9), and then dialyzed with PBS buffer. Finally, the hybridoma-derived antibody 125G4A4 was obtained for further characterization.

1.1 Detection of Binding Activities of Antibodies to CHO-K1 Cells Overexpressing Human CD47 Proteins by FACS A human CD47 protein (NCBI accession number: NP_001768.1) was overexpressed in hamster ovary cell line CHO-K1 to establish CHO-K1 cell line overexpressing the human CD47 protein. The cells were co-incubated with serially diluted antibody 125G4A4 and reference antibody C0774CK230-C (i.e., Hu5F9) (the highest concentration being 300 nM, three fold dilution, 12 concentration points in total) at 4° C. for 50 minutes. After washing twice with iced PBS, the cells were incubated with an iFluor647-labeled goat anti-mouse IgG (H+L) antibody (Genscript) at 4° C. in the dark for 40 minutes. The cells were washed twice with iced PBS, and then the fluorescence signal was detected by Calibur (BD Biosciences) flow cytometry, and according to the average fluorescence intensity (MFI) of the signal, GraphPad was used for fitting a concentration dependent curve, and the $EC_{50}$ was calculated. As shown in Table 1, the finally obtained hybridoma-derived antibody 125G4A4 has a high binding activity to CHO-K1 overexpressing human CD47 protein, with an $EC_{50}$ of 0.22 nM.

1.2 Detection of Binding Activities of Antibodies to CD47 on the Surface of Tumor Cells by FACS Human CD47 was endogenously expressed on the cell surface of human Burkitt lymphoma cell line Raji. The antibody 125G4A4 and the reference antibody Hu5F9 were serially diluted into PBS containing 2% fetal bovine serum (FBS, Gibco, Cat: 10100147) (the highest concentration being 46.3 nM, three fold dilution, 8 concentration points in total). The diluted antibodies were mixed with and co-incubated with Raji cells (purchased from ATCC) ($5*10^5$ cells/well) at 4° C. for 1 hour. After washing three times with PBS containing 2% fetal bovine serum (FBS), a PE-labeled mouse anti-human IgG Fc antibody (Biolegend, Cat: 409304) was added and incubated with the cells at 4° C. in the dark for 1 hour. The cells were washed three times with PBS containing 2% fetal bovine serum (FBS), and then the fluorescence signal was detected by CantoII (BD Biosciences) flow cytometry, and according to the average fluorescence intensity (MFI) of the signal, GraphPad was used for fitting a concentration dependent curve, and the $EC_{50}$ was calculated. As shown in Table 1, the hybridoma-derived antibody 125G4A4 has a binding activity to Raji cells, with an $EC_{50}$ of 0.84±0.02 nM.

1.3 Blockade of the Interaction Between Human CD47 and SIRPα by Anti-CD47 Antibodies ELISA assay was performed to detect the ability of 125G4A4 to block the interaction between human CD47 and SIRPα. The recombinant protein hCD47-Fc containing the extracellular domain of human CD47 fused with the Fc fragment of human IgG (ACROBiosystems, Cat: CD7-H5256) was coated onto a 96-well plate and incubated overnight at 4° C. After the plate was washed 3 times with PBST (PBS containing 0.5% Tween-20), PBST containing 1% BSA was added for blocking the plate for 2 hours. After the plate was washed three times with PBST, the mixture of serially diluted antibody 125G4A4 or reference antibody Hu5F9 (the highest concentration being 66.7 nM, three fold dilution, 8 concentration points in total) together with SIRPα-His recombinant protein (ACROBiosystems, Cat: SIA-5225) with a final concentration of 2.5 μg/ml was added and incubated at room temperature for 1 hour. The plate was washed three times with PBST, and a horseradish peroxidase labeled goat anti-His-tag secondary antibody (CWBIO, Cat: CW0285M) was added to detect SIRPα captured by coated CD47 protein. After the 96-well plate was incubated at 37° C. for 30 minutes, the plate was washed 5 times with PBST, and a TMD (Surmodics, Cat: TMBW-1000-01) developing solution was added, and was incubated in the dark for 15 minutes. 2N $H_2SO_4$ was added to terminate the color-developing reaction. $OD_{450}$ was read on a microplate reader. The absorbance value reflected the amount of SIRPα which bound to CD47. Graphpad was used for fitting a concentration dependent curve, and the $IC_{50}$ of anti-CD47 antibody for blocking binding of CD47 to SIRPα was calculated. As shown in Table 1, 125G4A4 can effectively block the CD47/SIRPα interaction, with an $IC_{50}$ of 3.06 nM.

1.4 Detection of Activity of Anti-CD47 Antibodies in Induction of Human Red Blood Cell Agglutination It is known that in the prior art, most of the anti-CD47 antibodies have the property of inducing red blood cell agglutination. It is widely believed that the property is closely related to clinical side effects such as anemia existing in the treatment by therapeutic anti-CD47 antibody. Therefore, we evaluate the anti-CD47 antibody in the present invention by a red blood cell agglutination experiment in vitro to screen the antibody without the property of inducing red blood cell agglutination. The method is as follows: collecting the healthy donor's fresh human blood, washing the cells five times with PBS, and then diluting the cells to make a suspension containing 10% human red blood cells; mixing the red blood cell suspension with the experimental antibody (antibody 125G4A4 and reference antibody Hu5F9, the highest concentration being 667 nM, three fold dilution, 12 concentration points in total), then adding the mixture into a round bottom 96-well plate; and incubating them at room temperature for 16 hours, then taking photos and determining the results according to the phenomenon of the cells in the well. If red blood cell agglutination occurs, cells are plated onto each well like a net, and a larger sheet-like cell layer will appear in the well with a diameter larger than that of the negative control well; on the contrary, if no hemagglutination occurs, the red blood cells will deposit at the bottom of the well, and smaller dot-like cell pellete precipitation will appear in the well. 125G4A4 shows no obvious phenomenon of inducing red blood cell agglutination in the experiment.

1.5 Determination of the Pro-Phagocytic Effects of Anti-CD47 Antibodies on Tumor Cells by Human Macrophages The ability of antibody 125G4A4 of the present invention to promote phagocytosis of tumor cells by macrophages was detected by assay based on flow cytometry. Human blood was freshly collected from healthy donors, and the peripheral blood mononuclear cells (PBMC) were isolated by density gradient centrifugation with Ficoll-Paque PLUS (GE Healthcare, Cat: 17-1440-02). Monocytes were further isolated and obtained by using the human total monocyte Isolation Kit (Miltenyi biotec, cat: 130-096-537). To induce the monocytes to differentiate into macrophages, macrophage colony stimulating factor (M-CSF, R & D Systems, Cat: 216-MC) was added and the monocytes was subjected to adherent culture for 7 consecutive days. On the day of cellular phagocytosis experiment, the above-mentioned differentiated macrophages were starved in a serum-free medium for 2 hours. At the same time, target tumor cells Raji were fluorescent labeled with CFSE (eBioscience, Cat: 65-0850-85) according to the steps recommended by the instructions. The CFSE-labeled tumor cells and macrophages were mixed in a ratio of 4:1, and the experimental antibodies of a detected concentration were added and incubated at 37° C. for 2 hours. Then the cells were washed twice with PBS, and then digested with trypsin (Gibco, Cat: 25200072); an APC labeled anti-CD14 antibody (Biolegend, Cat: 325608) was added and incubated in the dark on ice in PBS containing 2% fetal bovine serum for 30 minutes. The cells were washed twice and analyzed by flow cytometry. The percentage of CFSE positive cells in CD14 positive macrophage populations was calculated. As shown in Table 1, 125G4A4 can effectively promote the phagocytic function of macrophages on tumor cells.

TABLE 1

Determination of the Activity and function of hybridoma-derived antibody 125G4A4

| Clone number ID | Binding to CHO-K1 cells overexpressing human CD47 protein (FACS, $EC_{50}$, nM) | Binding to CD47 on the surface of Raji cells (FACS, $EC_{50}$, nM) (n = 3) | Blocking binding of SIRPα to human CD47 protein (ELISA, $IC_{50}$, nM) | Red blood cell agglutination test (0.03-66.7 nM) | Phagocytosis rate % of Raji (Antibody concentration: 33 nM) |
|---|---|---|---|---|---|
| Hu5F9 | 0.37 | 0.3 ± 0.01 | 1.55 | Positive (7.4-66.6 nM) | 36.5% |
| 125G4A4 | 0.22 | 0.84 ± 0.02 | 3.06 | Negative | 71.7% |

Example 2 Humanization of Hybridoma-Derived Antibody 2.1 Determination of Variable Region Sequence of Hybridoma-Derived Antibody According to the method for hybridoma sequencing, the cells of hybridoma clone 125G4A4 were subjected to an expanded culture; total RNA was extracted with TRIzol (purchased from Ambio) and reverse transcribed into DNA with antibody-specific primers (Takara, PrimerScript 1$^{st}$ Strand cDNA Synthesis Kit); and a gene fragment encoding mouse immunoglobulin V-region was subjected to amplification with antibody-specific primers. The variable region sequence of hybridoma-derived antibody was obtained by sequencing analysis. The amino acid sequences of the heavy chain variable region and the light chain variable region of the 125G4A4 antibody are as set forth in SEQ. ID Nos: 1 and 2, respectively, and the nucleotide sequences are as set forth in SEQ. ID Nos: 19 and 20, respectively.

2.2 Construction and Expression of Chimeric Antibodies

According to the mechanism of action of CD47, in a specific embodiment of the present invention, the constant region of human IgG4 (S228P) is used as the heavy chain constant region of the antibody, and the human κ light chain constant region chain is used as the light chain constant region of the antibody. Mutation of serine at position 228 of IgG4 core hinge region to proline (S228P) can enhance the disulfide bond connection in the core hinge region and reduce the exchange of IgG4 Fab arm, and thereby greatly reduce the formation of half molecules. After the genes encoding heavy chain and light chain constant regions were synthesized, the heavy chain and light chain variable region genes were homologously recombined into a vector PTT5 with double enzyme digestion by EcoRI and BamHI. After sequenced to be correct, the heavy chain and light chain of an antibody at a molar ratio of 1.5:1 are co-transfected into HEK293 cells. After 120 hours of culture, the supernatant was collected by centrifugation and purified to obtain a chimeric antibody.

Before humanization design, it is necessary to mutate some post translational modification (PTM) sites in the CDR region to avoid affecting the protein conformation, thereby affecting the function thereof. According to PTM analysis, two PTM sites in the CDR of 125G4A4 were identified, including one NSS glycosylation site in the heavy chain and one DG isomerization site in the light chain. The NSS glycosylation site and DG isomerization sites were mutated into QSS and EG, respectively. The mutated chimeric antibody obtained by purification in this example is named as Ch-125G4-m35. The amino acid sequences of the heavy chain variable region and the light chain variable region of Ch-125G4-m35 antibody are as set forth in SEQ. ID Nos: 3 and 4, respectively.

2.3 Humanized Design of Chimeric Antibodies

To select the human antibody backbone sequence with highest similarity to chimeric antibody 125G4A4m for humanization, the variable region sequence of chimeric antibody 125G4A4m was Blast aligned with the PDB Antibody database. The heavy chain variable region of 125G4A4 m has a higher sequence homology with human germline IGHV1-69, and the light chain variable region thereof has a higher sequence homology with human germline IGKV1-16. Then the amino acid sequence of the variable region CDR and the accurate boundary thereof are defined by the Kabat assignment system. Then, the CDR segments of the variable region of the murine antibody are grafted into the human backbone sequence to obtain the humanized antibody.

In order to maintain the activity of the humanized antibody, the framework amino acid sequences of the variable region and its surrounding region are analyzed with macromolecular docking analysis by using computer simulation technology to investigate their spatial stereoscopic binding mode. By calculating electrostatic force, van der Waals force, hydrophilicity and entropy, the key amino acid individuals that may interact with CD47 and maintain the spatial framework in the candidate antibody gene sequence are analyzed and grafted back to the selected human antibody gene framework. Meanwhile the amino acid positions in the framework region that must be reserved are marked. Based on the above process, the humanized antibody is synthesized. Some key sites in the antibody framework region were back mutated into the antibody framework region sequence of chimeric antibody Ch-125G4-m35. According to the number and arrangement of back mutations, a number of different humanized heavy chain variable regions (SEQ. ID No: 5, SEQ. ID No: 6, SEQ. ID No: 7) and light chain variable regions (SEQ. ID No: 8, SEQ. ID No: 9, SEQ. ID No: 10) were designed respectively (see Table 2). The finally determined humanized antibody Hu-125G4A4-48 of the present invention was named as HMA02h14-48 hereafter. The amino acid sequences of the heavy chain variable region and the light chain variable region of the antibody are as set forth in SEQ. ID Nos: 7 and 8, respectively.

TABLE 2

Number and arrangement of reverse mutations in 125G4A4m heavy chain and light chain

| Sequence number | Mutation number | Mutation site |
|---|---|---|
| Heavy chain variable region | | |
| SEQ. ID No.: 5 | 3 | E73K, S76R, S82aT |
| SEQ. ID No.: 6 | 4 | E73K, S76R, A78T, S82aT |
| SEQ. ID No.: 7 | 6 | V67A, I69L, E73K, S76R, A78T, S82aT |
| Light chain variable region | | |
| SEQ. ID No.: 8 | 1 | F71Y |
| SEQ. ID No.: 9 | 2 | T69Q, F71Y |
| SEQ. ID No.: 10 | 6 | Q3K, S46T, S60L, T69Q, F71Y, Y87F |

TABLE 3

Amino acid sequence of anti-CD47 antibody

| Antibody | Heavy chain variable region sequence | Light chain variable region sequence |
|---|---|---|
| 125G4A4 | SEQ. ID No.: 1 | SEQ. ID No.: 2 |
| ch-125G4-m35 | SEQ. ID No.: 3 | SEQ. ID No.: 4 |
| Hu-125G4A4m-43 | SEQ. ID No.: 6 | SEQ. ID No.: 9 |
| Hu-125G4A4m-44 | SEQ. ID No.: 6 | SEQ. ID No.: 10 |
| Hu-125G4A4m-45 | SEQ. ID No.: 5 | SEQ. ID No.: 8 |
| Hu-125G4A4m-46 | SEQ. ID No.: 5 | SEQ. ID No.: 9 |
| Hu-125G4A4m-47 | SEQ. ID No.: 5 | SEQ. ID No.: 10 |
| Hu-125G4A4m-48 | SEQ. ID No.: 7 | SEQ. ID No.: 8 |
| Hu-125G4A4m-49 | SEQ. ID No.: 7 | SEQ. ID No.: 9 |
| Hu-125G4A4m-50 | SEQ. ID No.: 7 | SEQ. ID No.: 10 |

TABLE 4

CDR amino acid sequences of anti-CD47 antibodies (Rabat definition)

| CDR | 125G4A4 | ch-125G4-m35 | HMA02h14-48 and variants thereof |
|---|---|---|---|
| HCDR1 | SEQ. ID No.: 11 | SEQ. ID No.: 11 | SEQ. ID No.: 11 |
| HCDR2 | SEQ. ID No.: 12 | SEQ. ID No.: 12 | SEQ. ID No.: 12 |
| HCDR3 | SEQ. ID No.: 13 | SEQ. ID No.: 17 | SEQ. ID No.: 17 |
| LCDR1 | SEQ. ID No.: 14 | SEQ. ID No.: 14 | SEQ. ID No.: 14 |
| LCDR2 | SEQ. ID No.: 15 | SEQ. ID No.: 18 | SEQ. ID No.: 18 |
| LCDR3 | SEQ. ID No.: 16 | SEQ. ID No.: 16 | SEQ. ID No.: 16 |

2.4 Expression of Humanized Antibodies

The DNA fragments encoding the above-mentioned designed humanized heavy chain and light chain variable regions were amplified and cloned into a vector comprising a constant region expressing a human antibody to construct an antibody-expressing plasmid (pCDNA3.4, purchased from Thermo Cat #A14697). The heavy and light chain expression vectors were co-transfected into Expire293 cells (Thermo Cat #A14525). After culturing at 37° C. for 6 days, the supernatant was collected. According to the above-mentioned method, the recombinant antibody was obtained by protein A affinity purification for further characterization of the antibody. The humanized antibody is IgG4 S228P (IgG4P) subtype.

Example 3 Screening of Humanized Antibodies

Highly active humanized antibodies were screened by detecting the binding ability of humanized antibodies to cynomolgus monkey B cells, the ability of human macrophages to phagocytose tumor cells and the ability of induction of red blood cell agglutination.

Detection of the binding ability of the humanized antibody to cynomolgus monkey B cells: flow cytometry method was used to detect the binding of a series of humanized 125G4A4 antibodies to CD47 on the surface of cynomolgus monkey B cells. The method is as follows: Peripheral blood mononuclear cells (PBMCs) were isolated from the blood of cynomolgus monkeys (provided by Shanghai Yinuosi Bio-Technology Co., Ltd.) by density gradient centrifugation with Ficoll-Paque PLUS (GE Healthcare, Cat: 17-1440-02). PBMC was incubated with a series of humanized 125G4A4 antibodies or isotypes control (IgG4P) in PBS containing 2% fetal bovine serum at 4° C. for 30 minutes. Then the cells were washed three times and incubated with the secondary antibody (PE-labeled mouse anti-human IgG Fc antibody, Biolegend, Cat: 409304) in PBS containing 2% fetal bovine serum at 4° C. in the dark for 30 minutes. The cells were washed three times and analyzed by flow cytometry. B cells were labeled with an anti-human CD20 antibody (Brilliant Violet 421™ labeled anti-human CD20 Antibody, Biolegend, Cat: 302330) having cross-reactivity with cynomolgus monkeys, and detected by flow cytometry on Canto II (BD Biosciences) to obtain its average fluorescence intensity (MFI).

According to the methods described in Examples 1.5 and 1.4, the ability of macrophages to phagocytose tumor cells and the ability of induction of red blood cell agglutination were detected respectively.

As shown in Table 5, a series of humanized 125G4A4 antibodies bind to CD47 expressed on cynomolgus monkey B cells under tested concentration. The antibodies promote phagocytosis of tumor cells Raji by macrophages, of which Hu-125G4A4m-48 displays the strongest phagocytic efficiency at 33 nM. The other activities of Hu-125G4A4m-48 are similar to those of chimeric antibody Ch-125G4m-m35. Moreover, the number of back mutations was smaller. Therefore, Hu-125G4A4m-48 was selected for further test, and was named as HMA02h14-48 hereafter.

TABLE 5

In vitro activity test of a series of anti-CD47 humanized antibodies

| | | Detection of binding efficiency to cynomolgus monkey B cells by FACS | | Phagocytosis rate % of Raji | | Red blood cell |
|---|---|---|---|---|---|---|
| Antibody | Reverse mutation number | Max MFI, Antibody test concentration 66.7 nM | Compared with Ch-125G4m-m35 value, % | Antibody test concentration 33 nM | Compared with Ch-125G4m-m35 value, % | agglutination Antibody test concentration 0.033-66.7 nM |
| Hu5F9 | — | 4118 | 90 | 18.3 | | Positive |
| Ch-125G4m-m35 | — | 4551 | 100 | 30.2 | 100 | Negative |
| Hu-125G4A4m-43 | 6 | 3259 | 72 | 33.8 | 112 | Negative |
| Hu-125G4A4m-44 | 10 | 4512 | 99 | 33.3 | 110 | Negative |
| Hu-125G4A4m-45 | 4 | 2634 | 58 | 28.8 | 95 | Negative |
| Hu-125G4A4m-46 | 5 | 2522 | 55 | 31.4 | 104 | Negative |
| Hu-125G4A4m-47 | 9 | 4100 | 90 | 32.1 | 106 | Negative |
| Hu-125G4A4m-48 | 7 | 4195 | 92 | 35.6 | 118 | Negative |
| Hu-125G4A4m-49 | 8 | 4079 | 90 | 35.1 | 116 | Negative |
| Hu-125G4A4m-50 | 12 | 4839 | 106 | 34.5 | 114 | Negative |
| isotype | — | 53 | — | 4.2 | — | Negative |

Example 4 Determination of Binding Activity of HMA02h14-48 to Tumor Cells by FACS Human CD47 is endogenously expressed on the surface of human Burkitt lymphoma cell line Raji cells (Shanghai Institutes for Biological Sciences, SIBS, CCL-86™/ATCC), human diffuse large cell lymphoma Toledo cells (ATCC® CRL-2631™) and human mantle cell lymphoma REC-1 cells (ATCC® CRL-3004™). According to the detection method described in the preceding Example 1.2, flow cytometry was used to detect the binding of the humanized antibody HMA02h14-48 to CD47 on the surface of the above-mentioned tumor cell lines. The highest antibody concentration was 667 nM, the antibodies were serially diluted, and a total of 8 concentration points were tested.

Figure 2:
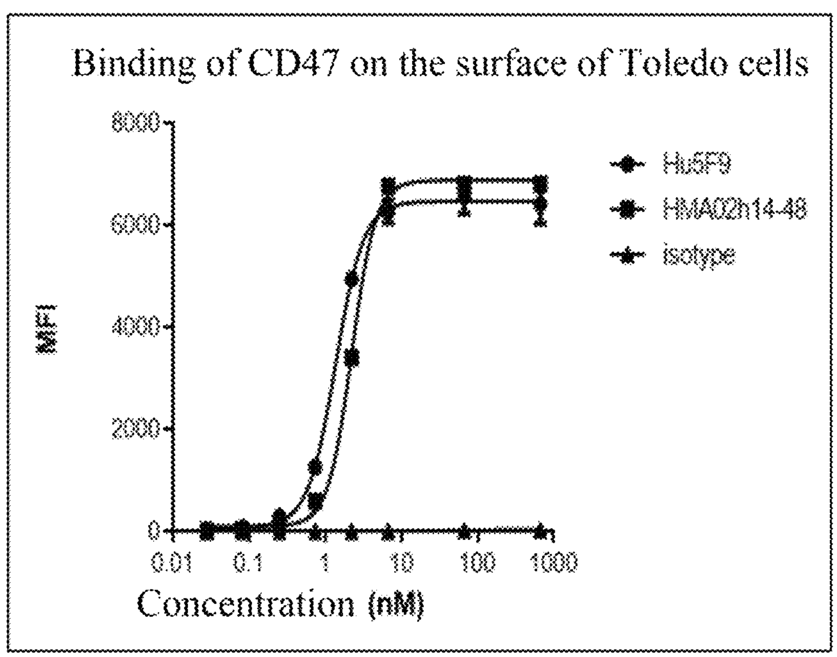
FIG. 2 shows the binding activity of antibody HMA02h14-48 to CD47 on the surface of Toledo cells.
Figure 3:
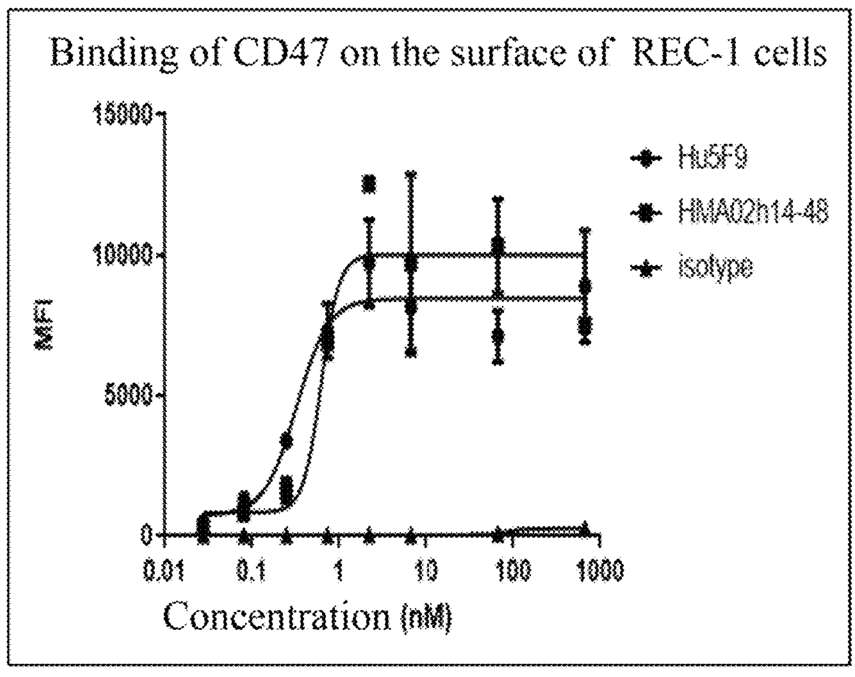
FIG. 3 shows the binding affinity of antibody HMA02h14-48 to CD47 on the surface of REC-1 cells.

As shown in FIGS. 1-3. Both HMA02h14-48 and Hu5F9 bound to CD47 on the surface of tumor cells, including Raji, Toledo and REC-1. The maximum fluorescence intensity when HMA02h14-48 reaches a plateau is higher than that of Hu5F9, and the $EC_{50}$ and the maximum fluorescence intensity are shown in Table 6.

TABLE 6

Binding activity of antibody HMA02h14-48 to CD47 on the surface of tumor cells

| | | isotype | HMA02h14-48 | Hu5F9 |
|---|---|---|---|---|
| Raji | $EC_{50}$ (nM) | / | 1.2 | 0.75 |
| | Max MFI | 175 | 7436 | 5958 |

TABLE 6-continued

Binding activity of antibody HMA02h14-48 to CD47 on the surface of tumor cells

| | | isotype | HMA02h14-48 | Hu5F9 |
|---|---|---|---|---|
| Toledo | $EC_{50}$ (nM) | / | 2.2 | 1.4 |
| | Max MFI | 50 | 6873 | 6703 |
| REC-1 | $EC_{50}$ (nM) | / | 0.6 | 0.3 |
| | Max MFI | 265 | 12629 | 10805 |

The negative isotype control antibody (isotype) used in this example and other examples was human IgG4P, which was purchased from Shanghai Chempartner Co., Ltd.

Example 5: Determination of Binding Affinity of Antibody HMA02h14-48 to Human CD47 by Biacore Biacore was used to determine the binding kinetic parameters by measuring surface plasmon resonance (SPR). This technology was used to detect the microscopic rate constants of the binding (ka) and dissociation (kd) of an antibody and an antigen. Based on the ka and kd values, the affinity value of the antibody and the antigen can be obtained. Both Biacore instrument (Biacore T200) and reagents were purchased from GE Healthcare. The anti-human Fc antibody was immobilized on sensor chip CM5. The purified antibodies (HMA02H14-48 and Hu5F9) were diluted in a mobile phase buffer (10 mM HEPES, 150 mM NaCl, 3 mM EDTA, 0.05% Tween-20, pH 7.4), and flowed through a CM5 chip coated with anti-human Fc antibodies. Then the serially diluted human CD47-His (ACROBiosystems, Cat: CD7-H5227) fusion protein flowed through a detection chip to measure the binding of the antigen and the antibody, and then the mobile phase buffer flowed through the chip to detect the dissociation of the antigen from the antibody. The binding and dissociation signal data of the antigen and the antibody were collected at different concentrations, and fitted at 1:1 by a Langmuir model to calculate the affinity of the antigen and the antibody.

As shown in Table 7, HMA02h14-48 binds to human CD47 with high affinity with a $K_D$ value of 7.77E-10 (M).

TABLE 7

Determination of kinetic constants of humanized antibody binding to human CD47 by Biacore

| Antibody | $k_a$ (1/Ms) | $k_d$ (1/s) | $K_D$ (M) |
|---|---|---|---|
| HMA02h14-48 | 8.34E+05 | 6.48E−03 | 7.77E−10 |
| Hu5F9 | 5.2E+07 | 1.01E−01 | 2.01E−09 |

Example 6 Detection of Activity of HMA02h14-48 in Blocking the Interaction Between Human CD47 and SIRPα by ELISA According to the method described in the preceding example 1.3, ELISA was used to detect the ability of HMA02h14-48 to block the interaction between human CD47 and SIRPα. The highest antibody concentration was 67 nM, the antibodies were serially diluted, and a total of 8 concentration points were tested.

Figure 4:
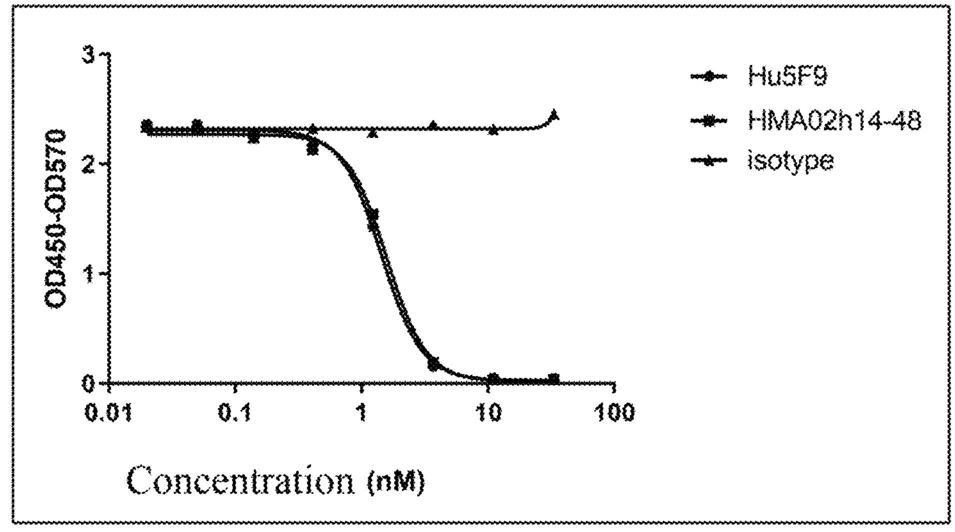
FIG. 4 shows the activity of antibody HMA02h14-48 in blocking the interaction between human CD47 and SIRPα.
Figure 5:
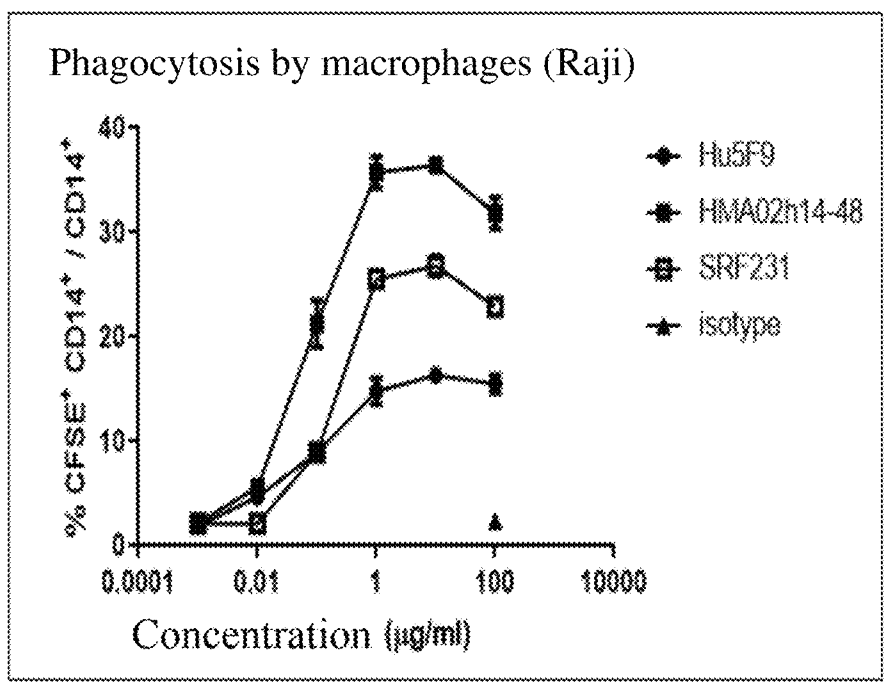
FIG. 5 shows the effect of antibody HMA02h14-48 on phagocytosis of Raji cells by human MΦ.
Figure 6:
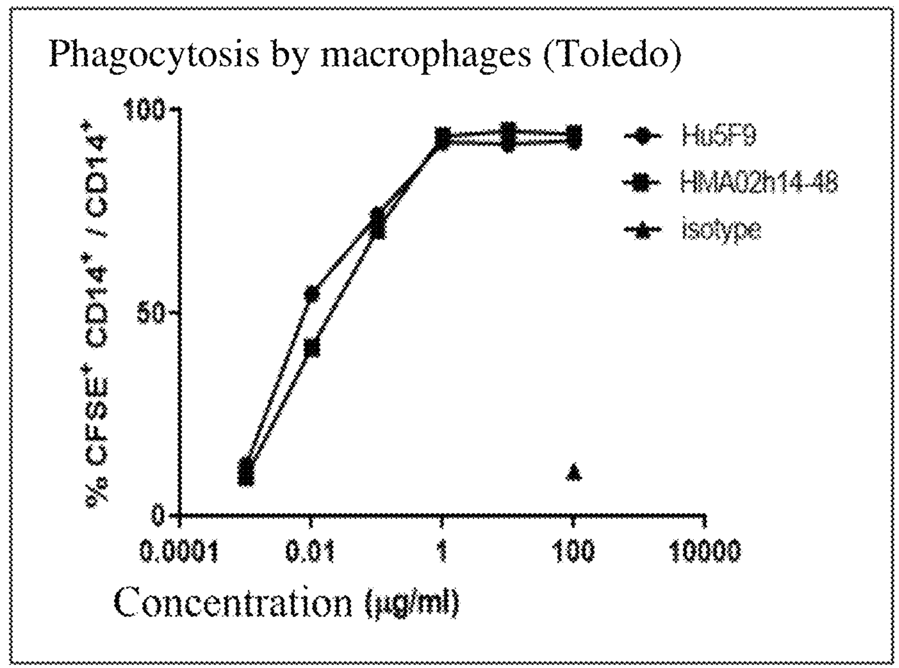
FIG. 6 shows the effect of antibody HMA02h14-48 on phagocytosis of Toledo cells by human MΦ.
Figure 7:
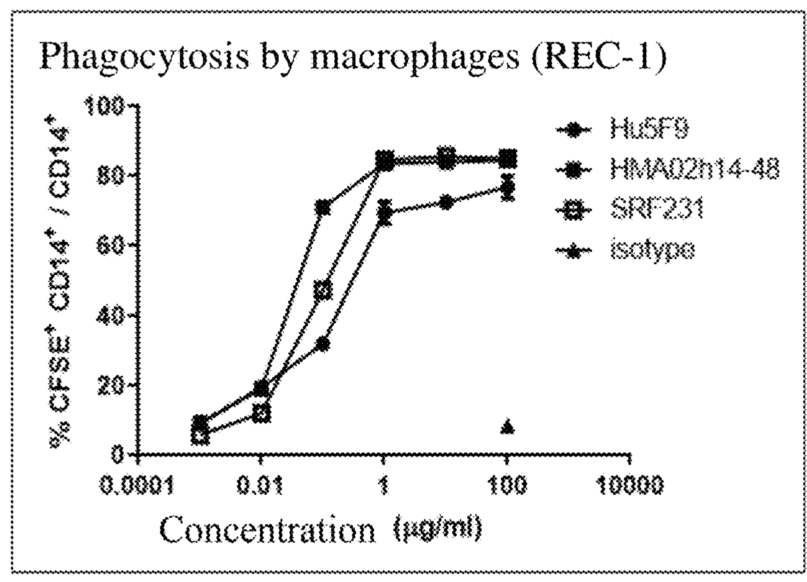
FIG. 7 shows the effect of antibody HMA02h14-48 on phagocytosis of REC-1 cells by human MΦ.
Figure 8:
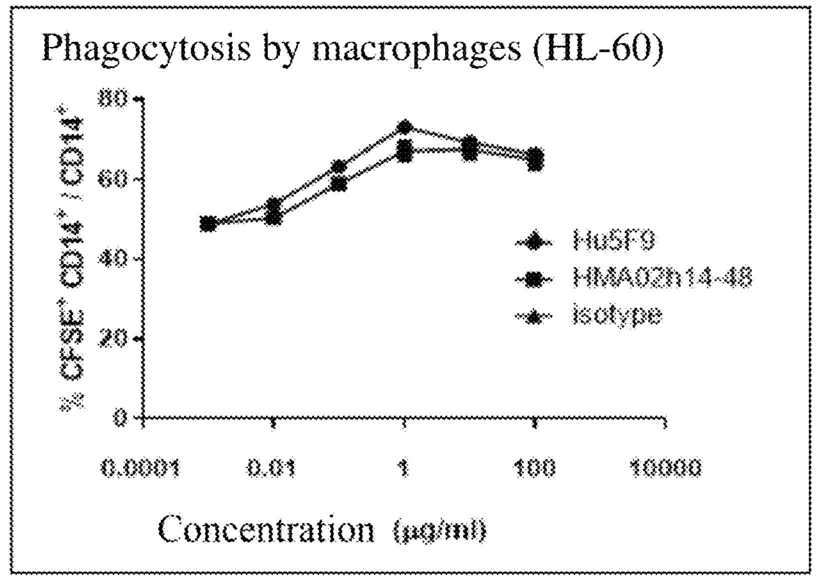
FIG. 8 shows the effect of antibody HMA02h14-48 on phagocytosis of HL-60 cells by human MΦ.

As shown in FIG. 4, the antibody HMA02h14-48 in the present invention blocks the interaction between human CD47 and SIRPα with $IC_{50}$=1.58 nM.

Example 7 Effects of HMA02h14-48 on Phagocytosis of Tumor Cells by Human Macrophages According to the method described in Example 1.5, the effect of HMA02h14-48 on promoting phagocytosis of human Burkitt lymphoma cell line Raji cells, human diffuse large cell lymphoma Toledo cells, human mantle cell lymphoma REC-1 cells and human promyelocytic leukemia cell line HL-60 cells by human macrophages was detected. The highest antibody concentration was 100 μg/mL, the antibodies were serially diluted, and a total of 8 concentration points were tested.

The results showed that compared with the reference antibodies Hu5F9 and SRF231, HMA02h14-48 could effectively promote the phagocytosis of human Burkitt lymphoma cell line Raji by macrophages. The highest phagocytic efficiency was up to 36.5%, and the phagocytosis rates at different concentrations from 0.1 to 100 μg/ml were higher than those of Hu5F9 and SRF231. The highest phagocytic efficiency of HMA02h14-48 for human mantle cell lymphoma REC-1 was up to 84.6%, and the phagocytosis rate could be maintained at about 70% even at a low concentration of 0.1 μg/ml, which was higher than those of Hu5F9 and SRF231. HMA02h14-48 promoted the phagocytosis of Toledo cells by macrophages, and the phagocytosis rate was up to 94.2%. HMA02h14-48 could promote the phagocytosis of tumor cell HL-60 by macrophages, and the highest phagocytic efficiency was up to 65%.

TABLE 8

Effect of antibody HMA02h14-48 for promoting phagocytosis of tumor cells by human MΦ

| | Phagocytosis rate (%) | | |
|---|---|---|---|
| | HMA02h14-48 | Hu5F9 | SRF231 |
| Toledo | | | |
| 100 | 94.0 | 92.5 | / |
| 10 | 94.2 | 91.8 | |
| 1 | 93.8 | 92.2 | |
| 0.1 | 73.9 | 74.2 | |
| 0.01 μg/mL | 43.5 | 54.8 | |
| isotype (100 μg/mL) | 11.3 | 11.3 | |
| Raji | | | |
| 100 | 31.9 | 15.5 | 22.9 |
| 10, | 36.5 | 16.4 | 26.8 |
| 1, | 35.8 | 14.8 | 25.6 |
| 0.1 | 21.3 | 9.0 | 9.0 |
| 0.01 μg/mL | 5.7 | 4.7 | 2.2 |
| isotype (100 μg/mL) | 2.4 | 2.4 | 2.4 |
| REC-1 | | | |
| 100 | 84.6 | 74.6 | 87.4 |
| 10 | 84.1 | 72.7 | 85.8 |
| 1 | 83.7 | 67.3 | 84.2 |
| 0.1 | 70.0 | 33.0 | 45.9 |
| 0.01 μg/mL | 19.2 | 19.6 | 19.6 |
| isotype (100 μg/mL) | 8.5 | 8.5 | 8.5 |
| HL-60 | | | |
| 100 | 65.0 | 66.3 | / |
| 10 | 67.6 | 69.3 | |
| 1 | 67.1 | 73 | |
| 0.01 μg/mL | 50.4 | 53.9 | |
| isotype (100 μg/mL) | 45.7 | 45.7 | |

Example 8 Detection of Effects of HMA02h14-48 on the Induction of Red Blood Cell Agglutination In Vitro Human red blood cells were diluted to 10% in PBS, and incubated with CD47 antibody added in a round bottom 96-well plate for 16 hours at room temperature. The presence of non-precipitated red blood cells is an evidence that proves red blood cell agglutination. Compared with the white dots formed by the precipitation of non-agglutinated red blood cells, the non-precipitated red blood cells could form a reticulated area which was larger than that of the negative isotype control antibody (see FIG. 9). The results of the negative isotype control antibody (Isotype) were used as normal standards.

According to the method described in Example 1.4, the antibody HMA0214-48 was tested to see whether it induces red blood cell agglutination. The highest antibody concentration was 667 nM, the antibodies were serially diluted, and a total of 12 concentration points were tested.

Figure 9:
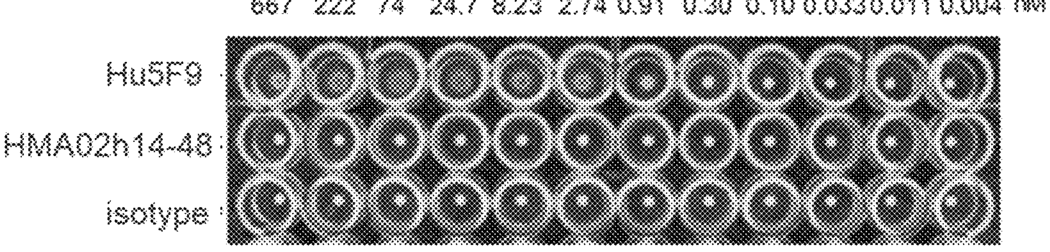
FIG. 9 shows the effect of antibody HMA02h14-48 on agglutination of the red blood cell in vitro.

As shown in FIG. 9, it showed that CD47 antibody Hu5F9 could significantly induce red blood cell agglutination when its concentration is 0.9 nM or above. By contrast, the antibody HMA02h14-48 in the present invention did not induce a significant hemagglutination of human red blood cells in vitro at different concentrations from 0.004 to 667 nM.

Example 9 Detection of Binding Activity of HMA02h14-48 to Human Red Blood Cells by FACS It is known that in the prior art, when therapeutic anti-CD47 antibodies are used clinically, side effects such as anemia often occur. It is generally believed that anti-CD47 antibodies bind to CD47 on the surface of red blood cells, which would in turn cause the phagocytosis of red blood cells by macrophages. This could be another major cause of anemia. In the present invention, flow cytometry was used to detect the binding ability of HMA02h14-48 to human red blood cells to evaluate the risk of antibodies. Specifically, red blood cells from healthy donors were incubated with diluted HMA02h14-48 (the maximum concentration being 667 nM, 8 test concentration points in total) in PBS containing 2% fetal bovine serum at 4° C. for 30 minutes. Then the cells were washed three times and incubated with the secondary antibody (PE-labeled mouse anti-human IgG Fc antibody, Biolegend, Cat: 409304) in PBS containing 2% fetal bovine serum at 4° C. in the dark for 30 minutes. The cells were washed three times with PBS containing 2% fetal bovine serum (FBS), and then the fluorescence signal was detected by Canto II (BD Biosciences) flow cytometry. According to the average fluorescence intensity (MFI) of the signal, GraphPad was used for fitting a concentration dependent curve, and the $EC_{50}$ was calculated.

Figure 10:
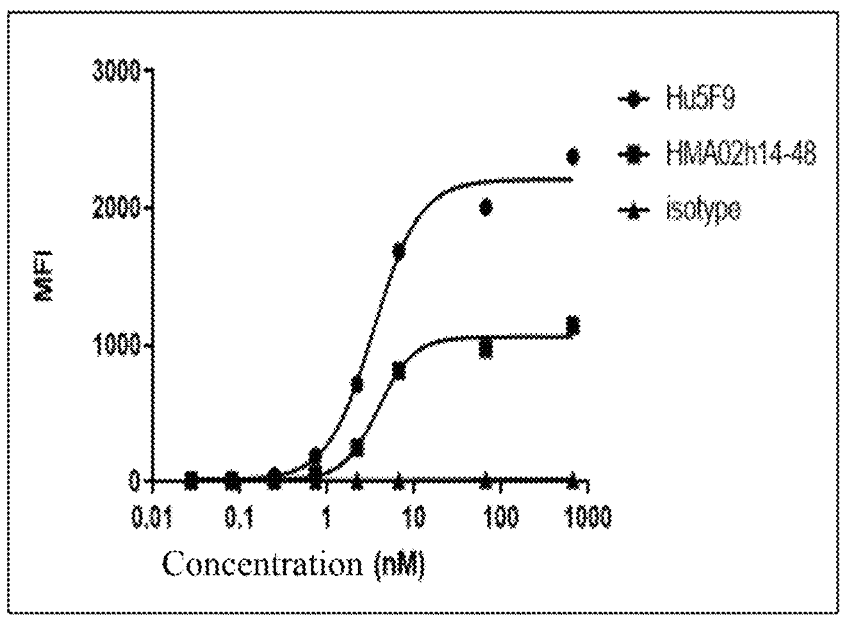
FIG. 10 shows the ability of antibody HMA02h14-48 to bind to CD47 on the surface of human red blood cells.

As shown in FIG. 10, the maximum mean fluorescence intensity of HMA02h14-48 bound to CD47 on the surface of human red blood cells was lower than that of control antibody Hu5F9. The maximum mean fluorescence intensity and $EC_{50}$ thereof was shown in Table 9.

TABLE 9

Binding activity of antibody HMA02h14-48 to CD47 on the surface of human red blood cells

| | HMA02h14-48 | Hu5F9 |
|---|---|---|
| $EC_{50}$ (nM) | 3.9 | 3.4 |
| Max MFI | 1165 | 2380 |

Example 10 Inhibition of Toledo Tumor Growth by Humanized Antibody HMA02h14-48

Objectives: A Toledo subcutaneous tumor model was established in NOD-Scid mice to study the anti-tumor activity of the antibody of the present invention.

Methods: human diffuse large B-cell lymphoma cells Toledo (ATCC® CRL-2631™) was cultured with RPMI1640 medium containing 10% fetal bovine serum. Tumor cells were suspended in RPMI1640 and implanted into male NOD-Scid mice (Shanghai Lingchang Biotechnology Co., Ltd.) subcutaneously in the right flank at a dose of $1\times10^7$ cells/mouse.

15 days after tumor cell inoculation, mice were randomly divided into 6 groups according to tumor volume, Hu5F9 and HMA02h14-48 antibodies were diluted with PBS respectively, and the mice were administered at a dose of 10 mg/kg according to the schedule shown in Table 10. The negative isotype control antibody (isotype) IgG4P was purchased from Shanghai ChemPartner Co., Ltd.

TABLE 10

Dosage regimens of Hu5F9 and HMA02h14-48

| Tested samples | Groups | Dose of administration (mg/kg × times) | Weekly total dose (mg/kg) | Dosage regimens | Number of mice |
|---|---|---|---|---|---|
| isotype | | 10 × 3 | 30 | Intraperitoneal injection on days 1, 4 and 7 | 6 |
| Hu5F9 | Hu5F9-H | 10 × 3 | 30 | Intraperitoneal injection on days 1, 4 and 7 | 6 |
| | Hu5F9-L | 10 × 1 | 10 | Intraperitoneal injection on day 1 | 6 |
| HMA02h14-48 | HMA-H | 10 × 3 | 30 | Intraperitoneal injection on days 1, 4 and 7 | 6 |
| | HMA-M | 10 × 2 | 20 | Intraperitoneal injection on days 1 and 4 | 6 |
| | HMA-L | 10 × 1 | 10 | Intraperitoneal injection on day 1 | 6 |

Note:
The grouping day is defined as day 0, and the next day for drug administration is day 1.

The tumor volumes (tumor volume=0.5×long diameter×short diameter$^2$) and body weights of the mice were measured regularly. The changes in tumor volume and body weight were statistically analyzed using student t-test in Excel software, wherein $p<0.05$ indicates a significant statistical difference. The tumor regression rate of each antibody treatment group after administration was calculated.

The formula for calculating tumor regression rate in each treatment group is: [($D_0$ average tumor volume−$D_t$ average tumor volume)/$D_0$ average tumor volume]×100%.

The formula for calculating the relative weight of a mouse is: (weight of the mouse on the day of measurement/weight of the mouse at the time of grouping)×100%.

Figure 11:
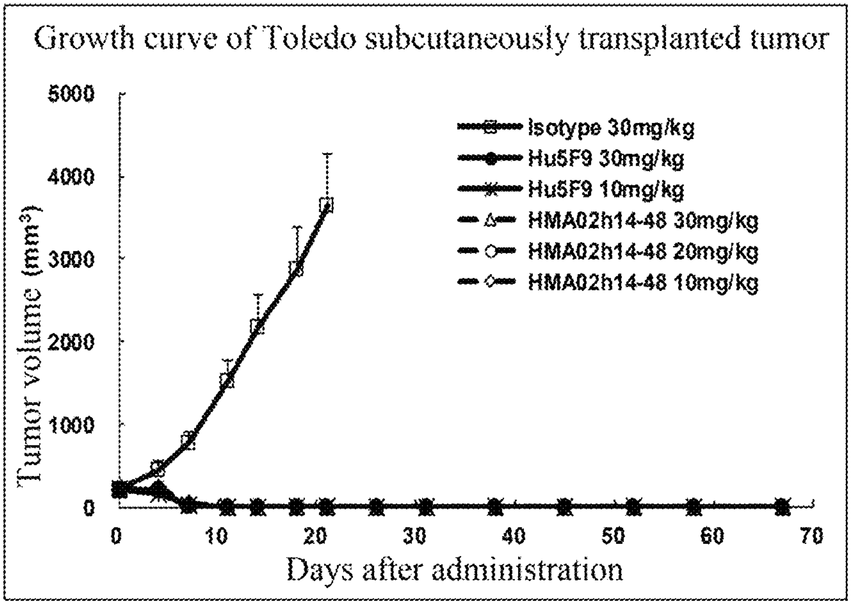
FIG. 11 shows the inhibition of Toledo tumor growth by Hu5F9 and HMA02h14-48.

Results:

The experimental results are shown in Table 11 and FIG. 11.

The tumors in the isotype control antibody group grew well, while in therapeutic antibody treatment groups, the subcutaneous tumor volume gradually reduced compared with the initial volume until completely regressed. Groups with Hu5F9 and HMA02h14-48 antibodies administered at various doses achieved the effect of complete tumor regression (regression rate of 100%) when measured on day 11, compared with the control antibody in the control group, the tumor volume reduction were statistically significant. After the dosing discontinuation, the animals were observed until day 67, and there was still no sign of tumor regrowth. In addition, the animals in groups with HMA02h14-48 administered at various doses were in good status, and there was no significant difference in the body weights of the mice on day 21 compared with that before treatment. The body weight of mice in the group with a high dose of Hu5F9 on day 21 was reduced by about 5% compared with that on day 0, but there was no statistical difference compared with the initial weight ($p>0.05$); however, there was no weight loss in the low-dose group of Hu5F9, suggesting a possible dose-related effect of Hu5F9 on body weight.

Based on the above-mentioned data, both Hu5F9 and HMA02h14-48 antibody treatments showed extremely significant anti-tumor effects. A single dose of either antibody at 10 mg/kg led to complete regression of the tumor and the duration is longa.

TABLE 11

Effect of Hu5F9 and HMA02h014-48 on Toledo subcutaneously transplanted tumor growth

| Groups | Number of animals (Start/ Day 21) | Tumor volume (mm$^3$) Day 0 | Day 11 | Day 21 | Relative body weight (%) Day 21 |
|---|---|---|---|---|---|
| Isotype | 6/6 | 199 ± 18 | 1524 ± 238 | 3646 ± 631 | 111.3 |
| Hu5F9-H | 6/6 | 200 ± 23 | 0 ± 0** (100%) | 0 ± 0** (100%) | 94.5 |
| Hu5F9-L | 6/6 | 196 ± 14 | 0 ± 0** (100%) | 0 ± 0** (100%) | 100.3 |
| HMA-H | 6/6 | 199 ± 26 | 0 ± 0** (100%) | 0 +± 0** (100%) | 99.1 |
| HMA-M | 6/6 | 199 ± 24 | 0 ± 0** (100%) | 0 ± 0** (100%) | 100.3 |
| HMA-L | 6/6 | 199 ± 18 | 0 ± 0** (100%) | 0 ± 0** (100%) | 100.4 |

Note:
**is $p < 0.01$; The numbers in parentheses are tumor regression rates.

Example 11 Inhibition of REC-1 Tumor Growth by Humanized Antibody HMA02h14-48

Objectives: a REC-1 subcutaneous tumor model was established in NOD-Scid mice to study the anti-tumor activity of the antibody of the present invention.

Methods: human mantle cell lymphoma cells REC-1 (ATCC® CRL-3004™) was cultured in RPMI1640 medium containing 10% fetal bovine serum. Tumor cells were suspended in RPMI1640 and implanted into male NOD-Scid mice (Shanghai Lingchang Biotechnology Co., Ltd.) subcutaneously in the right flank at a dose of $5\times10^6$ cells/mouse.

11 days after tumor cell inoculation, mice were randomly divided into 5 groups according to tumor volume, Hu5F9 and HMA02h14-48 antibodies were diluted with PBS, and the mice were administered according to the schedule shown in Table 12. The antibody Hu5F9 was prepared by GenScript, and the antibody HMA02h14-48 was prepared according to the method in Example 2. The isotype control antibody (isotype) IgG4p was purchased from Shanghai ChemPartner Co., Ltd.

TABLE 12

Dosing regimens of Hu5F9 and HMA02h14-48

| Tested samples | Groups | Dose of adminis-tration (mg/kg × times) | Total dose (mg/ kg) | Dosage regimens | Number of mice |
|---|---|---|---|---|---|
| | Isotype | 10 × 1 | 10 | Intraperitoneal injection on day 1 | 6 |
| Hu5F9 | Hu5F9-M | 3 × 1 | 3 | Intraperitoneal injection on day 1 | 6 |
| HMA02h14-48 | HMA-L | 1 × 1 | 1 | Intraperitoneal injection on day 1 | 6 |
| | HMA-M | 3 × 1 | 3 | Intraperitoneal injection on day 1 | 6 |
| | HMA-H | 10 × 1 | 10 | Intraperitoneal injection on day 1 | 6 |

Note:
The grouping day is defined as day 0, and the next day for drug administration is day 1.

The tumor volumes (tumor volume=0.5×long diameter×short diameter$^2$), and body weights of the mice were measured regularly. The tumor inhibition rate and regression rate of the antibody treatment group on day 12 after administration were calculated.

The formula for calculating tumor inhibition rate is as follows: [(average tumor volume change in the control group-average tumor volume change in the treatment group)/average tumor volume change in the control group]×100%. The changes in tumor volume and body weight were statistically analyzed using Student t-test in Excel software, wherein $p<0.05$ indicates a significant statistical difference.

The formula for calculating tumor regression rate in each treatment group is: [($D_0$ average tumor volume−$D_t$ average tumor volume)/$D_0$ average tumor volume]×100%.

The formula for calculating the relative weight of a mouse is: (weight of the mouse on the day of measurement/weight of the mouse at the time of grouping)×100%.

Figure 12:
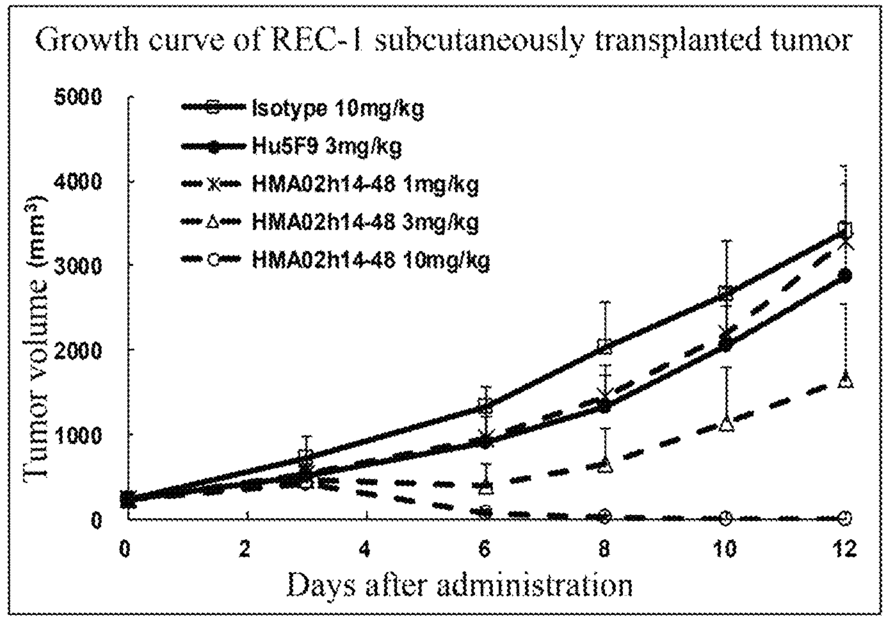
FIG. 12 shows the inhibition of REC-1 tumor growth by Hu5F9 and HMA02h14-48.

Results:

The experimental results were shown in Table 13 and FIG. 12.

12 days after administration, compared with Isotype group, the tumor growth inhibition rate was 16.7% ($p>0.05$) in the group treated with a single dose of Hu5F9 at 3 mg/kg; and the tumor growth inhibition rates were 3.8% ($p>0.05$), 54.7% ($p<0.01$) and 107.2% ($p<0.001$), respectively, in the groups with a single dose of HMA02h14-48 at 1 mg/kg, 3 mg/kg and 10 mg/kg. Groups treated with a high dose of HMA02h14-48 antibody achieved complete tumor regression (regression rate of 100%) on day 10. In addition, there was no significant difference in the relative body weight of the mice in different treatment groups.

Taken together, HMA02h14-48 antibody showed dose-dependent effect in REC-1 model, and a single dose of 10 mg/kg led to complete tumor regression.

TABLE 13

Effect of Hu5F9 and HMA02h14-48 on REC-1 subcutaneously implanted tumor growth

| Groups | Number of animals (Start/ Day 12) | Tumor volume ($mm^3$) Day 0 | Tumor volume ($mm^3$) Day 12 | Tumor inhibition rate (%) Day 12 | Relative body weight (%) Day 12 |
|---|---|---|---|---|---|
| Isotype-10 mg/kg | 6/6 | 226 ± 50 | 3403 ± 570 | — | 111.8 |
| Hu5F9-3 mg/kg | 6/6 | 227 ± 49 | 2875 ± 659 | 16.7 | 112.1 |
| HMA02h14-48-1 mg/kg | 6/6 | 225 ± 36 | 3283 ± 889 | 3.8 | 111.0 |
| HMA02h14-48-3 mg/kg | 6/6 | 224 ± 52 | 1664 ± 890 | 54.7** | 109.7 |
| HMA02h14-48-10 mg/kg | 6/6 | 228 ± 65 | 0 ± 0 (100%) | 107.2** | 101.2 |

Note:
**is $p < 0.01$; The numbers in parentheses are tumor regression rates.

Sequences of the Present Invention:

| | |
|---|---|
| SEQ. ID No.: 1 | QVQLQQSGTELAKPGASVKMSCKASGYTFTSYYMHWVKQRPGQILEWIGYIDPANDYSDYNQNFK DKATLTADKSSRTTYMQLTSLTSEDSAVYYCARLGYGNSSPFDYWGQGTTLIVSS |
| SEQ. ID No.: 2 | DIKMTQSPSSMYASVGERVTITCKASQDIHNYLSWFQQKPGKSPKTLIYRAKRLVDGVPLRFSGS GSGQDYSLTISSLEYEDMGIYFCLQYDELYTFGGGTRLEIK |
| SEQ. ID No.: 3 | QVQLQQSGTELAKPGASVKMSCKASGYTFTSYYMHWVKQRPGQILEWIGYIDPANDYSDYNQNFK DKATLTADKSSRTTYMQLTSLTSEDSAVYYCARLGYGQSSPFDYWGQGTTLIVSS |
| SEQ. ID No.: 4 | DIKMTQSPSSMYASVGERVTITCKASQDIHNYLSWFQQKPGKSPKTLIYRAKRLVEGVPLRFSGS GSGQDYSLTISSLEYEDMGIYFCLQYDELYTFGGGTRLEIK |
| SEQ. ID No.: 5 | QVQLVQSGAEVKKPGSSVKVSCKASGYTFTSYYMHWVRQAPGQGLEWMGYIDPANDYSDYNQNFK DRVTITADKSTRTAYMELTSLRSEDTAVYYCARLGYGQSSPFDYWGQGTTVTVSS |
| SEQ. ID No.: 6 | QVQLVQSGAEVKKPGSSVKVSCKASGYTFTSYYMHWVRQAPGQGLEWMGYIDPANDYSDYNQNFK DRVTITADKSTRTTYMELTSLRSEDTAVYYCARLGYGQSSPFDYWGQGTTVTVSS |
| SEQ. ID No.: 7 | QVQLVQSGAEVKKPGSSVKVSCKASGYTFTSYYMHWVRQAPGQGLEWMGYIDPANDYSDYNQNFK DRATLTADKSTRTTYMELTSLRSEDTAVYYCARLGYGQSSPFDYWGQGTTVTVSS |
| SEQ. ID No.: 8 | DIQMTQSPSSLSASVGDRVTITCKASQDIHNYLSWFQQKPGKAPKSLIYRAKRLVEGVPSRFSGS GSGTDYTLTISSLQPEDFATYYCLQYDELYTFGQGTRLEIK |
| SEQ. ID No.: 9 | DIQMTQSPSSLSASVGDRVTITCKASQDIHNYLSWFQQKPGKAPKSLIYRAKRLVEGVPSRFSGS GSGQDYTLTISSLQPEDFATYYCLQYDELYTFGQGTRLEIK |
| SEQ. ID No.: 10 | DIKMTQSPSSLSASVGDRVTITCKASQDIHNYLSWFQQKPGKAPKTLIYRAKRLVEGVPLRFSGS GSGQDYTLTISSLQPEDFATYFCLQYDELYTFGQGTRLEIK |
| SEQ. ID No.: 11 | SYYMH |
| SEQ. ID No.: 12 | YIDPANDYSDYNQNFKD |
| SEQ. ID No.: 13 | LGYGNSSPFDY |
| SEQ. ID No.: 14 | KASQDIHNYLS |
| SEQ. ID No.: 15 | RAKRLVD |
| SEQ. ID No.: 16 | LQYDELYT |
| SEQ. ID No.: 17 | LGYGQSSPFDY |
| SEQ. ID No.: 18 | RAKRLVE |
| SEQ. ID No.: 19 | CAGGTCCAGCTTCAGCAGTCTGGGACTGAACTGGCAAAACCCGGGGCCTCAGTGAAGATGTCCTG CAAGGCTTCTGGGTACACGTTTACTAGTTATTATATGCACTGGGTAAAACAGAGGCCTGGACAAA TTCTGGAGTGGATTGGATACATTGATCCTGCCAATGATTATAGTGACTACAATCAGAATTTCAAG GACAAGGCCACATTGACTGCAGACAAATCCTCCAGGACAACCTACATGCAACTGACCAGCCTGAC ATCTGAGGACTCTGCAGTCTATTATTGTGCAAGATTGGGCTACGGTAATAGCTCCCCTTTTGACT ACTGGGGCCAAGGCACCACTCTCATAGTATCTTCA |
| SEQ. ID No.: 20 | GACATCAAGATGACCCAGTCTCCATCTTCCATGTATGCATCTGTAGGAGAGAGAGTCACTATCAC TTGCAAGGCGAGTCAGGACATTCATAACTATTTAAGTTGGTTCCAGCAGAAACCAGGGAAATCTC CTAAGACCCTGATCTATCGTGCAAAAAGATTGGTAGATGGGGTCCCATTAAGGTTCAGTGGCAGT GGATCTGGGCAAGATTATTCTCTCACCATCAGCAGCCTGGAGTATGAAGATATGGGAATTTATTT TTGTCTACAGTATGATGAGTTGTACACGTTCGGAGGGGGGACCAGGCTGGAAATAAAA |

-continued

| | |
|---|---|
| SEQ ID NO: 21 | LGYGXSSPFDY (X can be any amino acid, preferably N or Q or H, D, K, R or E, or a conservative amino acid thereof) |
| SEQ ID NO: 22 | RAKRLVX (X can be any amino acid, preferably D or E or N or Q, or a conservative amino acid thereof) |

The invention claimed is:

1. An isolated anti-CD47 antibody or antigen-binding fragment thereof, comprising:

three of heavy chain complementary determining region 1 (HCDR1), HCDR2, and HCDR3, comprised in a heavy chain variable region (VH); and three of light chain complementary determining region 1 (LCDR1), LCDR2, and LCDR3, comprised in a light chain variable region (VL); wherein the VH and VL are selected from:

(1) a VH comprising the amino acid sequence as set forth in SEQ ID NO: 7, and a VL comprising the amino acid sequence as set forth in SEQ ID NO: 8, 9 or 10;

(2) a VH comprising the amino acid sequence as set forth in SEQ ID NO: 1, and a VL comprising the amino acid sequence as set forth in SEQ ID NO: 2;

(3) a VH comprising the amino acid sequence as set forth in SEQ ID NO: 3, and a VL comprising the amino acid sequence as set forth in SEQ ID NO: 4;

(4) a VH comprising the amino acid sequence as set forth in SEQ ID NO: 5, and a VL comprising the amino acid sequence as set forth in SEQ ID NO: 8, 9 or 10; or (5) a VH comprising the amino acid sequence as set forth in SEQ ID NO: 6, and a VL comprising the amino acid sequence as set forth in SEQ ID NO: 9 or 10.

2. An isolated anti-CD47 antibody or antigen-binding fragment thereof, comprising:

a heavy chain variable region (VH) comprising heavy chain complementary determining region 1 (HCDR1), HCDR2 and HCDR3, wherein the HCDR1 comprises or consists of the amino acid sequence as set forth in SEQ ID NO: 11, the HCDR2 comprises or consists of the amino acid sequence as set forth in SEQ ID NO: 12, and the HCDR3 comprises or consists of the amino acid sequence as set forth in SEQ ID NO: 17 or 13; and a light chain variable region (VL) comprising light chain complementary determining region 1 (LCDR1), LCDR2 and LCDR3, wherein the LCDR1 comprises or consists of the amino acid sequence as set forth in SEQ ID NO: 14, the LCDR2 comprises or consists of the amino acid sequence as set forth in SEQ ID NO: 18 or 15, and the LCDR3 comprises or consists of the amino acid sequence as set forth in SEQ ID NO: 16.

3. The isolated anti-CD47 antibody or antigen-binding fragment thereof of claim 2, wherein:

(1) the HCDR1 comprises the amino acid sequence as set forth in SEQ ID NO: 11, the HCDR2 comprises the amino acid sequence as set forth in SEQ ID NO: 12, and the HCDR3 comprises the amino acid sequence as set forth in SEQ ID NO: 17; and the LCDR1 comprises the amino acid sequence as set forth in SEQ ID NO: 14, the LCDR2 comprises the amino acid sequence as set forth in SEQ ID NO: 18, and the LCDR3 comprises the amino acid sequence as set forth in SEQ ID NO: 16; or (2) the HCDR1 comprises the amino acid sequence as set forth in SEQ ID NO: 11, the HCDR2 comprises the amino acid sequence as set forth in SEQ ID NO: 12, and the HCDR3 comprises the amino acid sequence as set forth in SEQ ID NO: 13; and the LCDR1 comprises the amino acid sequence as set forth in SEQ ID NO: 14, the LCDR2 comprises the amino acid sequence as set forth in SEQ ID NO: 15, and the LCDR3 comprises the amino acid sequence as set forth in SEQ ID NO: 16.

4. The isolated anti-CD47 antibody or antigen-binding fragment thereof of claim 3, comprising:

(1) a heavy chain variable region (VH) comprising an amino acid sequence identical to or having at least 90%, 91%, 92%, 93%, 94%, 95%, 96%, 97%, 98% or 99% sequence identity to the amino acid sequence as set forth in SEQ ID NO: 1, 3, 5, 6 or 7; and (2) a light chain variable region (VL) comprising an amino acid sequence identical to or having at least 90%, 91%, 92%, 93%, 94%, 95%, 96%, 97%, 98% or 99% sequence identity to the amino acid sequence as set forth in SEQ ID NO: 2, 4, 8, 9 or 10.

5. The isolated anti-CD47 antibody or antigen-binding fragment thereof of claim 4, wherein the VH comprises the amino acid sequence as set forth in any one of SEQ ID NOs: 1, 3, 5, 6 and 7, and the VL comprises the amino acid sequence as set forth in any one of SEQ ID NOs: 2, 4, 8, 9 and 10.

6. The isolated anti-CD47 antibody or antigen-binding fragment thereof of claim 5, comprising a heavy chain variable region (VH) and a light chain variable region (VL), wherein the VH and VL are selected from:

(1) a VH comprising the amino acid sequence as set forth in SEQ ID NO: 7; and a VL comprising the amino acid sequence as set forth in SEQ ID NO: 8, 9 or 10;

(2) a VH comprising the amino acid sequence as set forth in SEQ ID NO: 1; and a VL comprising the amino acid sequence as set forth in SEQ ID NO: 2;

(3) a VH comprising the amino acid sequence as set forth in SEQ ID NO: 3; and a VL comprising the amino acid sequence as set forth in SEQ ID NO: 4;

(4) a VH comprising the amino acid sequence as set forth in SEQ ID NO: 5; and a VL comprising the amino acid sequence as set forth in SEQ ID NO: 8, 9 or 10; and (5) a VH comprising the amino acid sequence as set forth in SEQ ID NO: 6; and a VL comprising the amino acid sequence as set forth in SEQ ID NO: 9 or 10.

7. The isolated anti-CD47 antibody or antigen-binding fragment thereof of claim 6, comprising a heavy chain variable region (VH) and a light chain variable region (VL), wherein the VH comprises the amino acid sequence as set forth in SEQ ID NO: 7, and the VL comprises the amino acid sequence as set forth in SEQ ID NO: 8.

8. The isolated anti-CD47 antibody or antigen-binding fragment thereof of claim 3, comprising a heavy chain constant region.

9. The isolated anti-CD47 antibody or antigen-binding fragment thereof of claim 3, comprising a light chain constant region.

10. The isolated anti-CD47 antibody or antigen-binding fragment thereof of claim 3, which is a murine antibody, a chimeric antibody or a humanized antibody.

11. The isolated anti-CD47 antibody or antigen-binding fragment thereof of claim 3, which is a full-length antibody, a Fab, a Fab', a Fab'-SH, a $(Fab')_2$, a scFv, a Fv, or a bis (multi)-specific antibody.

12. An isolated nucleic acid, encoding the isolated anti-CD47 antibody or antigen-binding fragment thereof of claim 3.

13. A recombinant vector or an expression vector, comprising one or more nucleic acids encoding the isolated anti-CD47 antibody or antigen-binding fragment thereof of claim 3, wherein the vector is suitable for the recombinant production of the isolated anti-CD47 antibody or antigen-binding fragment thereof of claim 3.

14. A host cell, comprising one or more recombinant vectors or expression vectors of claim 13.

15. An immunoconjugate or immune fusion, comprising the isolated anti-CD47 antibody or antigen-binding fragment thereof of claim 3.

16. A pharmaceutical composition, comprising:

(i) the isolated anti-CD47 antibody or antigen-binding fragment thereof of claim 3, or (ii) an isolated nucleic acid, encoding the isolated anti-CD47 antibody or antigen-binding fragment thereof of claim 3, or (iii) a recombinant vector or an expression vector, comprising one or more nucleic acids encoding the isolated anti-CD47 antibody or antigen-binding fragment thereof of claim 3, wherein the vector is suitable for the recombinant production of the isolated anti-CD47 antibody or antigen-binding fragment thereof of claim 3, or (iv) a host cell, comprising one or more recombinant vectors or expression vectors according to (iii), or (v) an immunoconjugate or immune fusion, comprising the isolated anti-CD47 antibody or antigen-binding fragment thereof of claim 3;

and wherein the pharmaceutical composition further comprises a pharmaceutically acceptable excipient.

17. A method for treating a CD47-expressing cancer, comprising administering to an individual an effective amount of the isolated anti-CD47 antibody or antigen-binding fragment thereof of claim 3.

18. The method of claim 17, wherein the cancer is selected from a hematological cancer and a solid tumor.

19. The antibody or antigen-binding fragment thereof of claim 8, wherein the heavy chain constant region is a human IgG1 constant region, a human IgG1TM constant region, a human IgG4 constant region or a human IgG4P constant region.

20. The antibody or antigen-binding fragment thereof of claim 9, wherein the light chain constant region is a human κ light chain constant region.

21. The method of claim 17, wherein the cancer is selected from bladder cancer, pancreatic cancer, lymphoma, leukemia, multiple myeloma, (malignant) melanoma, liomyoma, leiomyosarcomas, glioma, glioblastoma, myeloma, endometrial cancer, renal carcinoma, (benign) melanoma, prostate cancer, thyroid carcinoma, cervical cancer, gastric cancer, liver cancer, colon cancer, ovarian cancer, and urothelial carcinoma.

22. The isolated anti-CD47 antibody or antigen-binding fragment thereof of claim 2, wherein:

(1) the HCDR1 consists of the amino acid sequence as set forth in SEQ ID NO: 11, the HCDR2 consists of the amino acid sequence as set forth in SEQ ID NO: 12, and the HCDR3 consists of the amino acid sequence as set forth in SEQ ID NO: 17; and the LCDR1 consists of the amino acid sequence as set forth in SEQ ID NO: 14, the LCDR2 consists of the amino acid sequence as set forth in SEQ ID NO: 18, and the LCDR3 consists of the amino acid sequence as set forth in SEQ ID NO: 16; or (2) the HCDR1 consists of the amino acid sequence as set forth in SEQ ID NO: 11, the HCDR2 consists of the amino acid sequence as set forth in SEQ ID NO: 12, and the HCDR3 consists of the amino acid sequence as set forth in SEQ ID NO: 13; and the LCDR1 consists of the amino acid sequence as set forth in SEQ ID NO: 14, the LCDR2 consists of the amino acid sequence as set forth in SEQ ID NO: 15, and the LCDR3 consists of the amino acid sequence as set forth in SEQ ID NO: 16.

* * * * *